United States Patent
Kitazawa et al.

(10) Patent No.: US 9,841,812 B2
(45) Date of Patent: Dec. 12, 2017

(54) IMAGE DISPLAY DEVICE AND INFORMATION INPUT DEVICE

(71) Applicant: Sony Corporation, Tokyo (JP)

(72) Inventors: Yuji Kitazawa, Tokyo (JP); Seiji Wada, Kanagawa (JP); Kota Aizawa, Tokyo (JP); Yutaka Fukuyama, Kanagawa (JP)

(73) Assignee: Sony Corporation (JP)

( * ) Notice: Subject to any disclaimer, the term of this patent is extended or adjusted under 35 U.S.C. 154(b) by 126 days.

(21) Appl. No.: 14/437,690

(22) PCT Filed: Sep. 11, 2013

(86) PCT No.: PCT/JP2013/005380
§ 371 (c)(1),
(2) Date: Apr. 22, 2015

(87) PCT Pub. No.: WO2014/068832
PCT Pub. Date: May 8, 2014

(65) Prior Publication Data
US 2015/0301594 A1    Oct. 22, 2015

(30) Foreign Application Priority Data

Nov. 2, 2012    (JP) .................................. 2012-243065

(51) Int. Cl.
*G09G 5/00*    (2006.01)
*G06F 3/01*    (2006.01)
(Continued)

(52) U.S. Cl.
CPC ............ *G06F 3/013* (2013.01); *A61B 5/0488* (2013.01); *A61B 5/0496* (2013.01);
(Continued)

(58) Field of Classification Search
None
See application file for complete search history.

(56) References Cited

U.S. PATENT DOCUMENTS 5,360,971 A    11/1994  Kaufman et al.
5,621,424 A *   4/1997  Shimada .............. G02B 27/017
                                                    345/8
(Continued)

FOREIGN PATENT DOCUMENTS

GB    2281838 A    3/1995
JP    2000-023065 A    1/2000
(Continued)

OTHER PUBLICATIONS

Robert Krupiaa Ski et al: 11 Estimation of Eye Blinking Using Biopotentials Measurements for Computer Animation ApplicationS, Nov. 10, 2008 (Nov. 10, 2008). Computer Vision and Graphics, Springer Berlin Heidelberg, Berlin, Heidelberg, pp. 302-310, XP019119681,ISBN: 978-3-642-02344-6.

(Continued)

*Primary Examiner* — Ifedayo Iluyomade
(74) *Attorney, Agent, or Firm* — Lerner, David, Littenberg, Krumholz & Mentlik, LLP

(57) ABSTRACT

According to an illustrative embodiment, an information processing device is provided. The information processing device includes at least one electrode configured to generate at least one signal related to eye blinking of a subject; and a processing circuit configured to receive the at least one signal and detect eye blinking of the subject based on the at least one signal.

15 Claims, 22 Drawing Sheets

(51) Int. Cl.
*A61B 5/0488* (2006.01)
*A61B 5/0496* (2006.01)
*A61B 5/11* (2006.01)
*A61B 5/00* (2006.01)
*G06F 3/0482* (2013.01)
*G02B 27/01* (2006.01)
*A61B 3/113* (2006.01)
*A61B 5/04* (2006.01)

(52) U.S. Cl.
CPC .......... *A61B 5/1103* (2013.01); *A61B 5/6814* (2013.01); *G02B 27/01* (2013.01); *G06F 3/0482* (2013.01); *A61B 3/113* (2013.01); *A61B 5/04012* (2013.01)

(56) References Cited

U.S. PATENT DOCUMENTS

| | | | | |
|---|---|---|---|---|
| 5,991,085 | A * | 11/1999 | Rallison | G02B 27/017 345/8 |
| 7,639,146 | B2 | 12/2009 | Baura | |
| 9,007,301 | B1 * | 4/2015 | Raffle | G09G 3/003 345/156 |
| 2006/0077064 | A1 * | 4/2006 | Baura | A61B 5/0492 340/575 |
| 2011/0071416 | A1 * | 3/2011 | Terada | A61B 5/0478 600/544 |
| 2012/0162764 | A1 | 6/2012 | Shimizu | |
| 2013/0257709 | A1 * | 10/2013 | Raffle | G06F 3/017 345/156 |
| 2013/0278631 | A1 * | 10/2013 | Border | G02B 27/017 345/633 |

FOREIGN PATENT DOCUMENTS

| | | |
|---|---|---|
| JP | 2001-133724 A | 5/2001 |
| JP | 2005-086328 A | 3/2005 |
| JP | 2011-125693 A | 6/2011 |
| JP | 2012-138654 A | 7/2012 |
| WO | 2004-021157 A1 | 3/2004 |

OTHER PUBLICATIONS

Harry Septanto et al: 11A computer cursor controlled by eye movements and voluntary eye winks using a single channel EOG 11,Electrical Engineering and Informatics, 2009. ICEEI •09. International Conference on, IEEE, Piscataway, NJ, USA,Aug. 5, 2009 (Aug. 5, 2009), pp. 117-120, XP031530102, ISBN: 978-1-4244-4913-2.

International Search Report from International Publication No. PCT/JP2013/005380 dated Dec. 9, 2013.

Harry Septanto et al: 11 A computer cursor controlled by eye movements and voluntary eye winks using a single channel EOG 11,Electrical Engineering and Informatics, 2009. ICEEI •09. International Conference on, IEEE, Piscataway, NJ, USA,Aug. 5, 2009 (Aug. 5, 2009), pp. 117-120, XP031530102, ISBN: 978-1-4244-4913-2.

* cited by examiner

[Fig. 1]
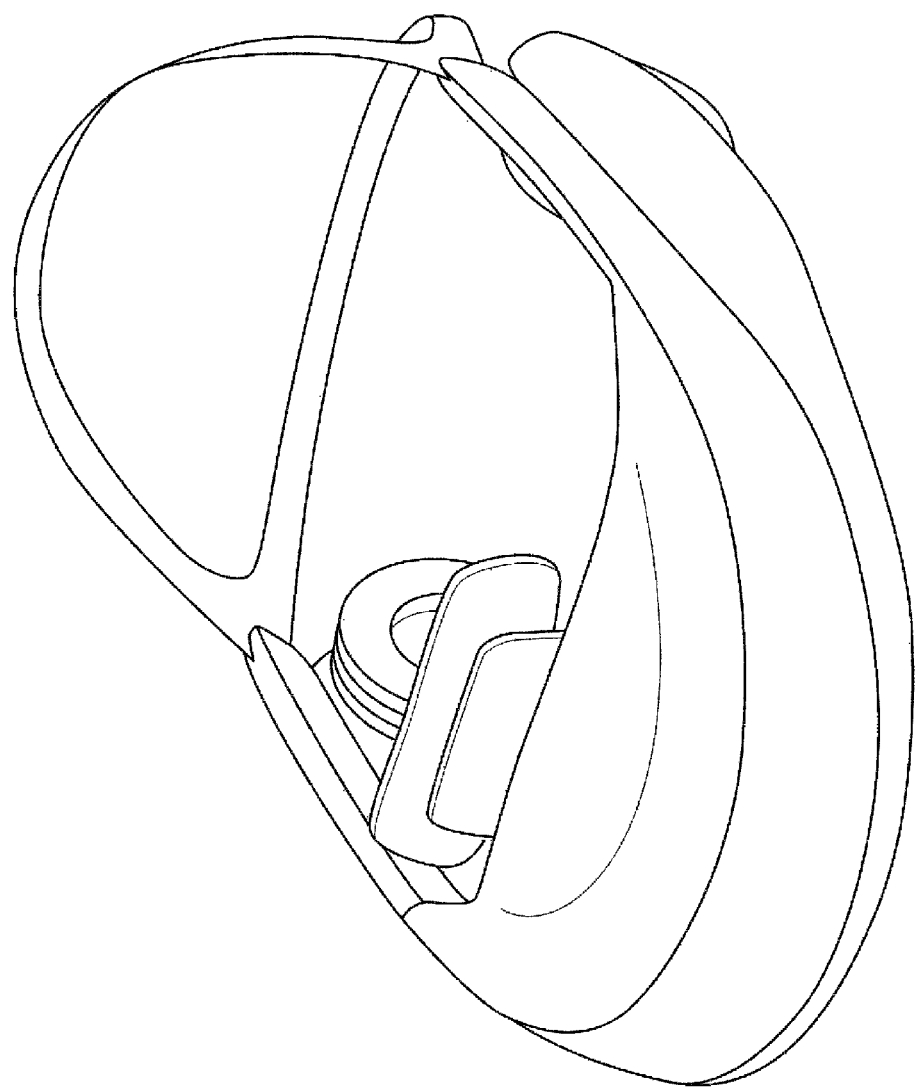

[Fig. 2]
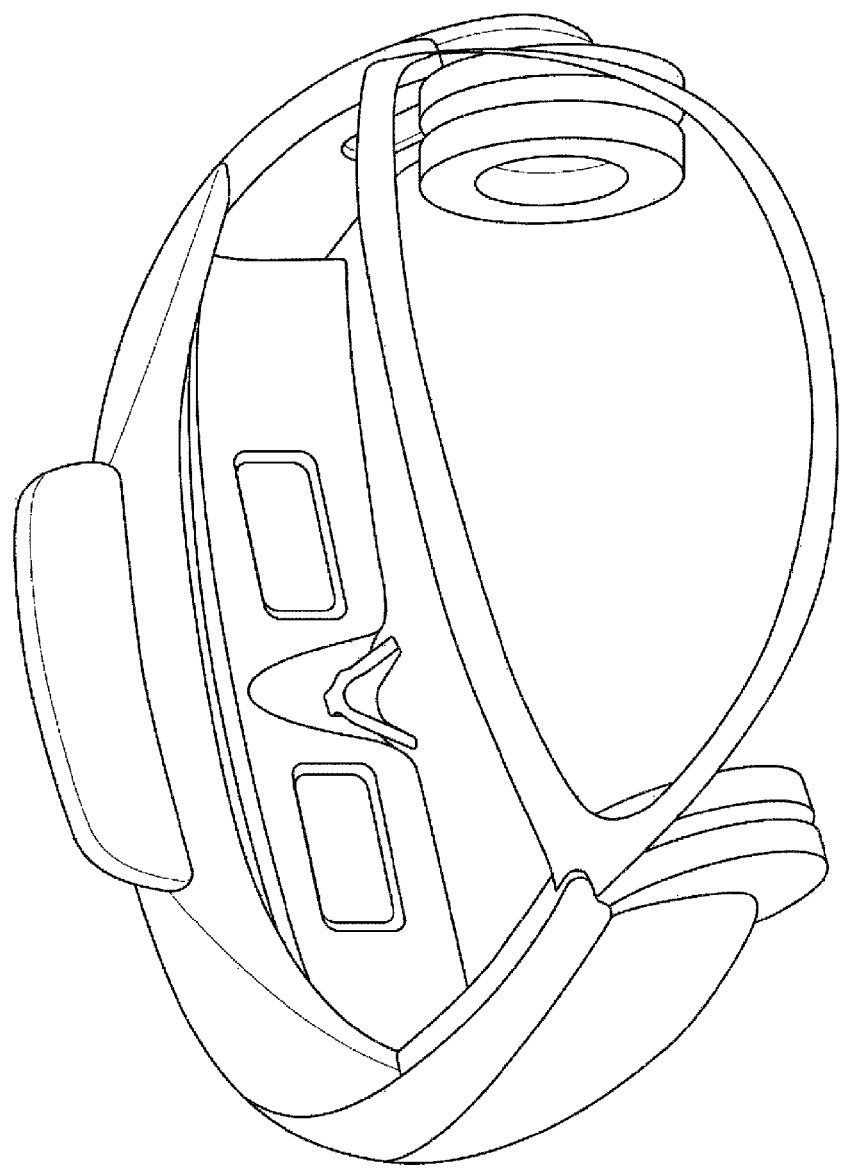

[Fig. 3]
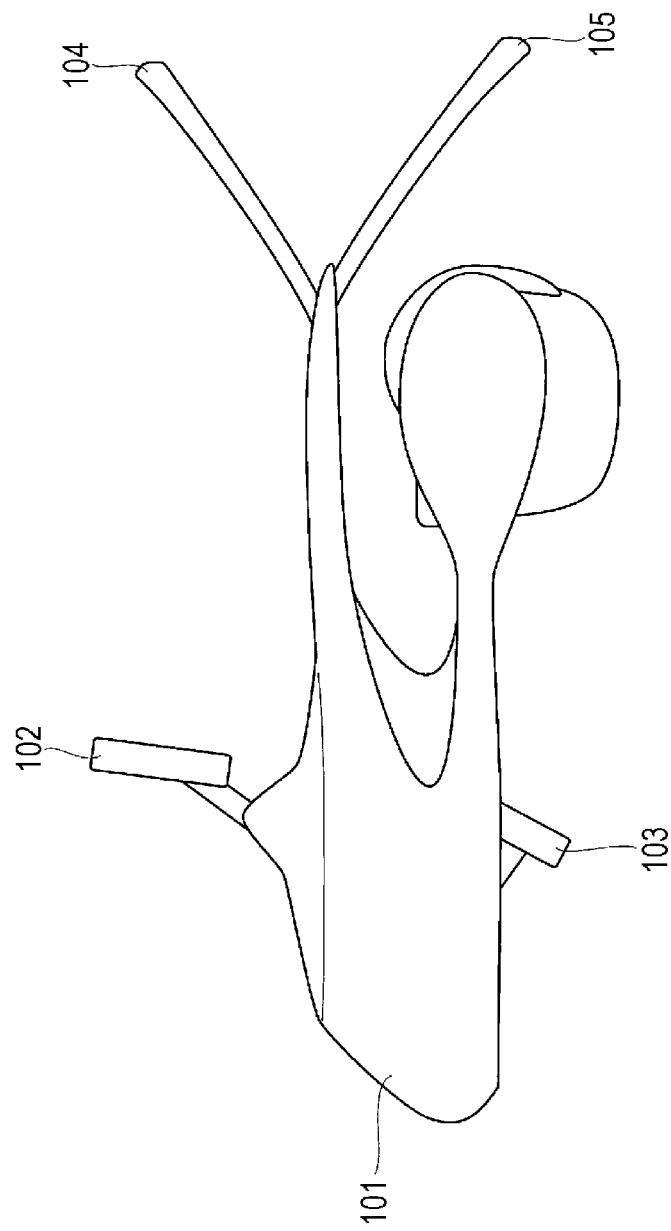

[Fig. 4]
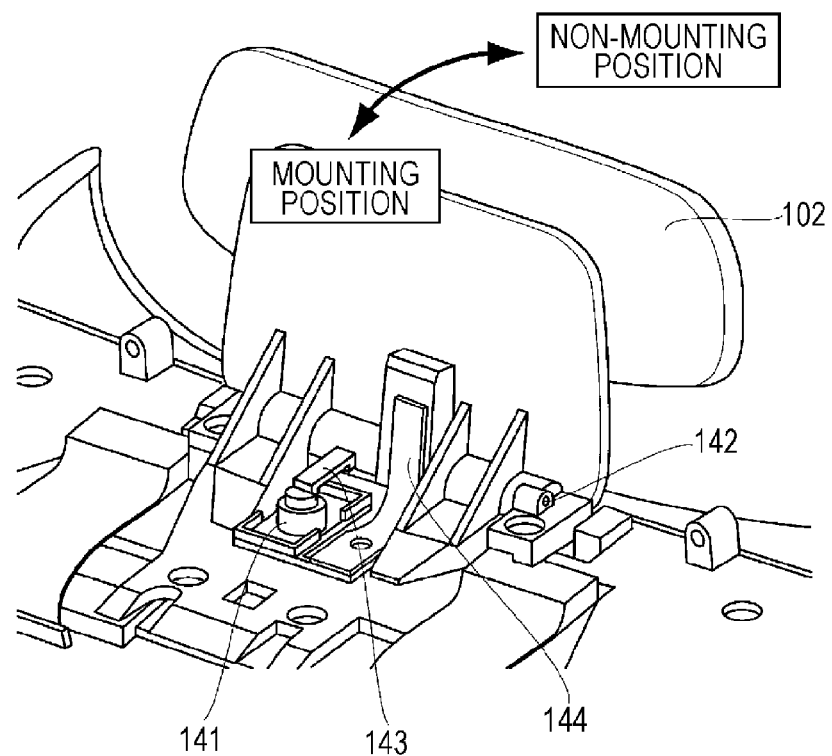
[Fig. 5]
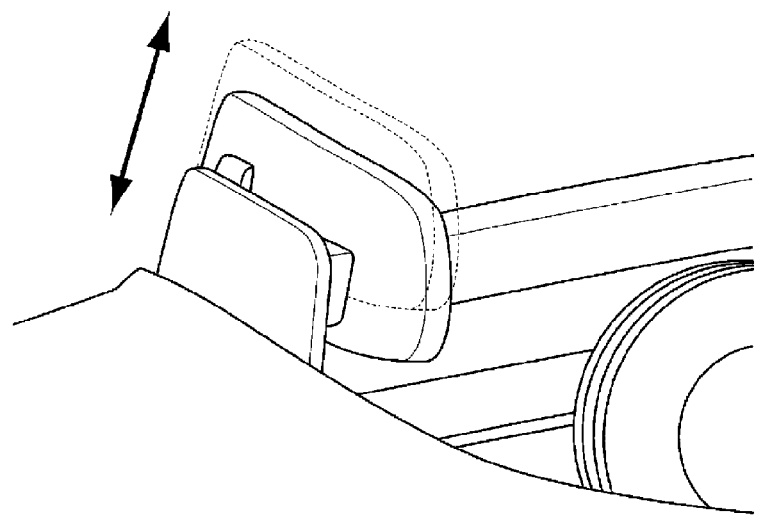

[Fig. 6]
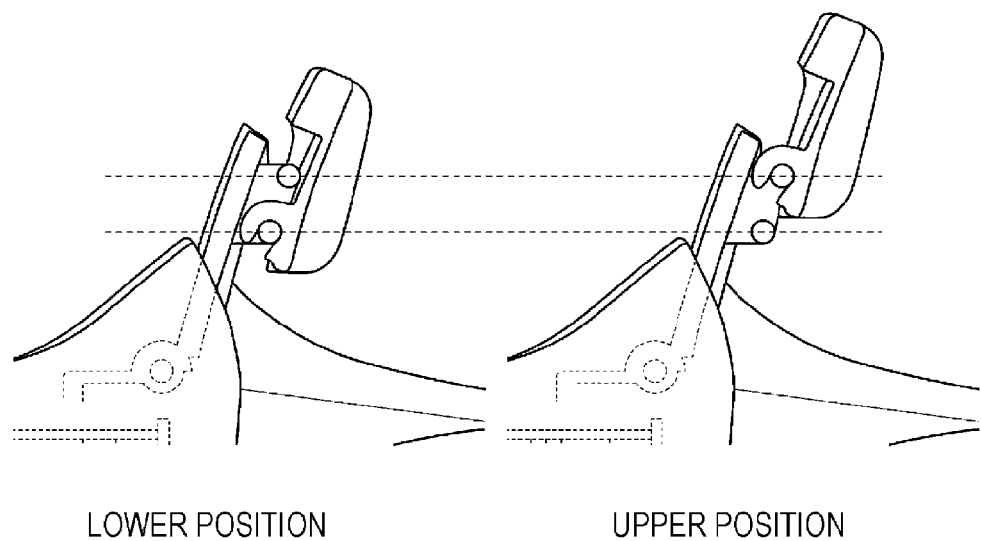
LOWER POSITIONUPPER POSITION

[Fig. 7]
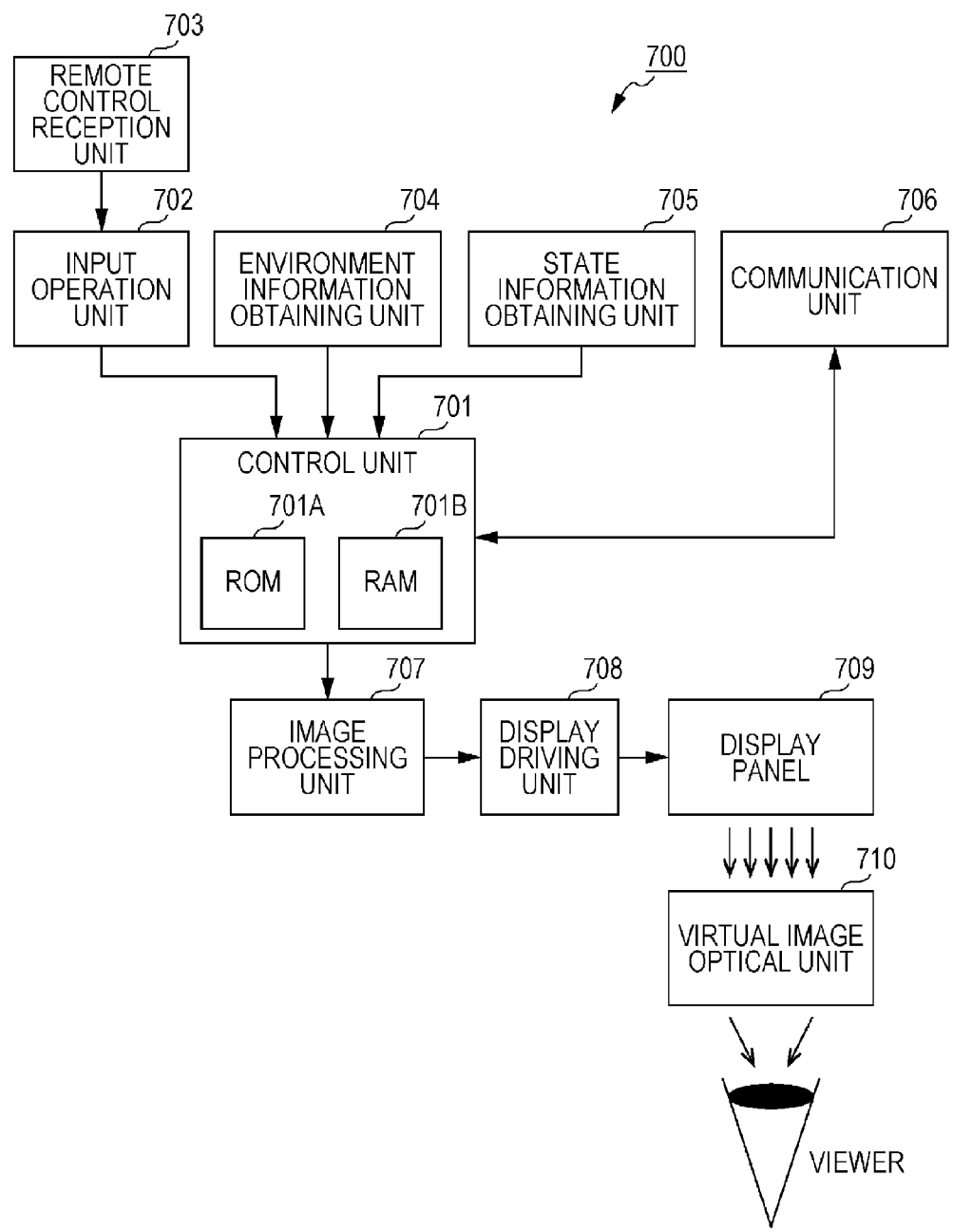

[Fig. 8]
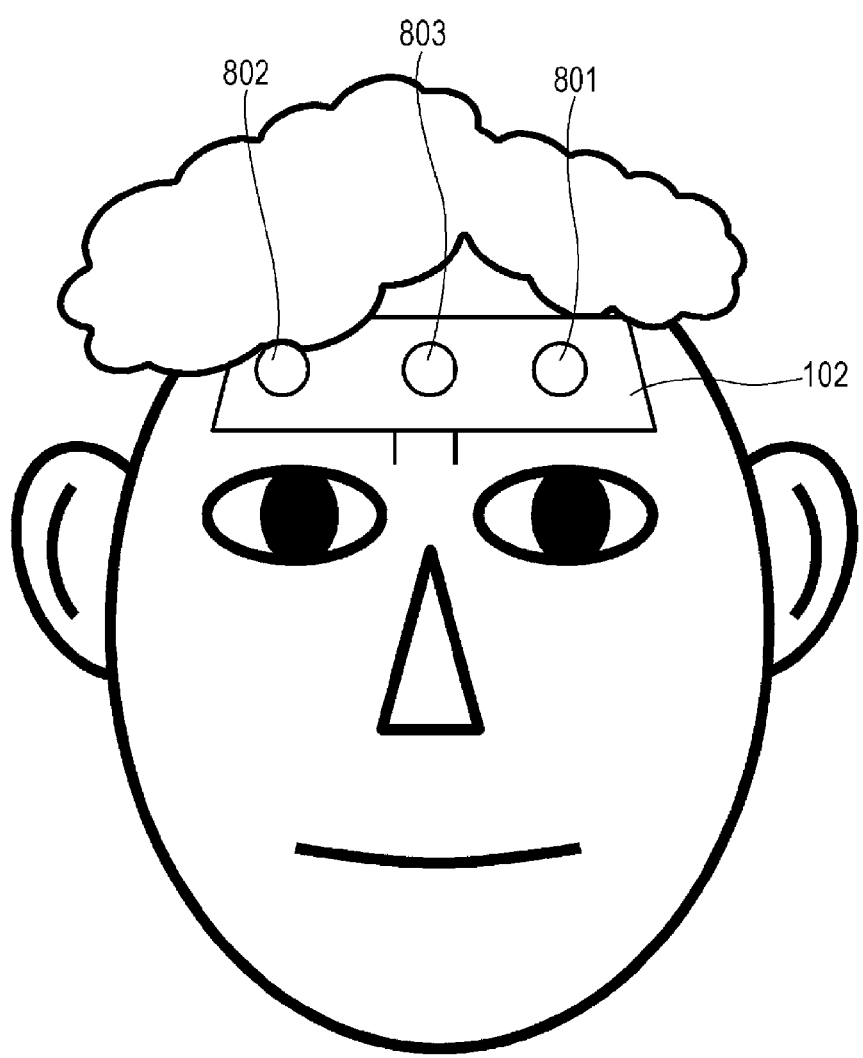

[Fig. 9]
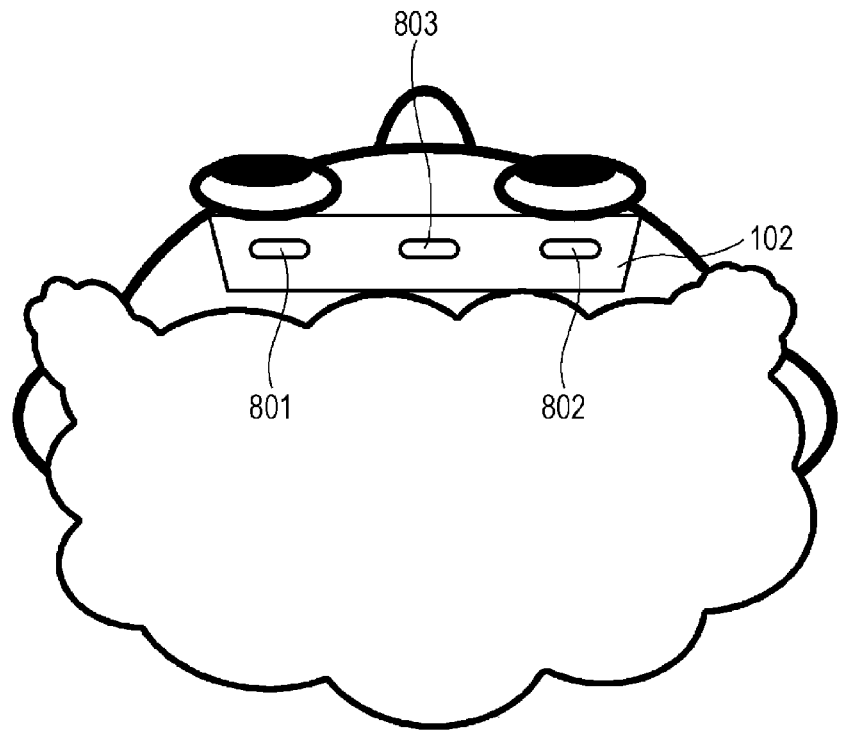
[Fig. 10]
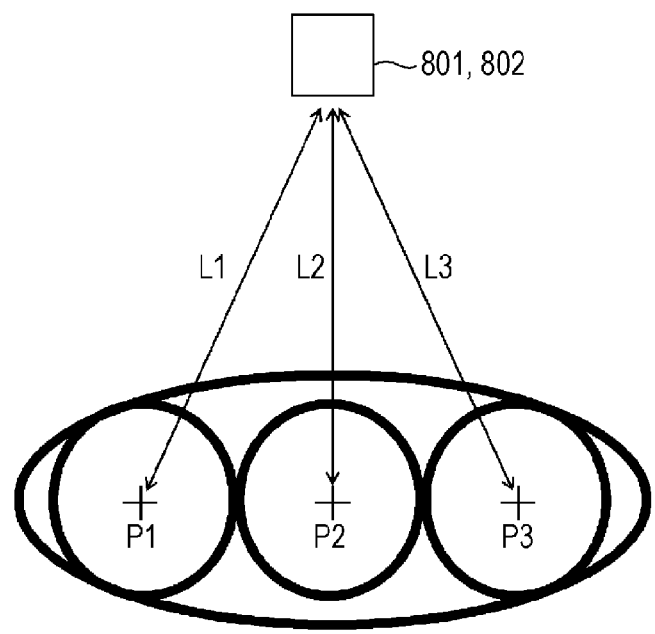

[Fig. 11]
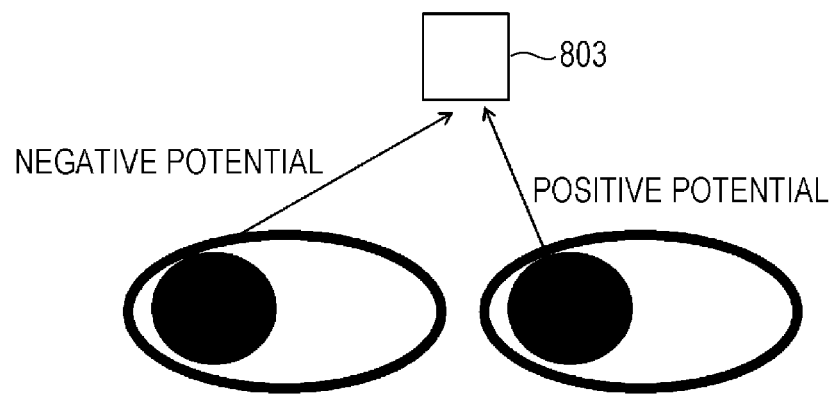
[Fig. 12]
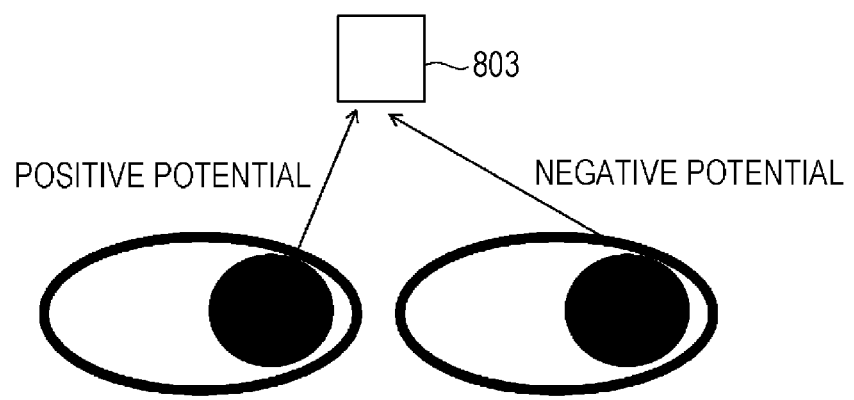

[Fig. 13]
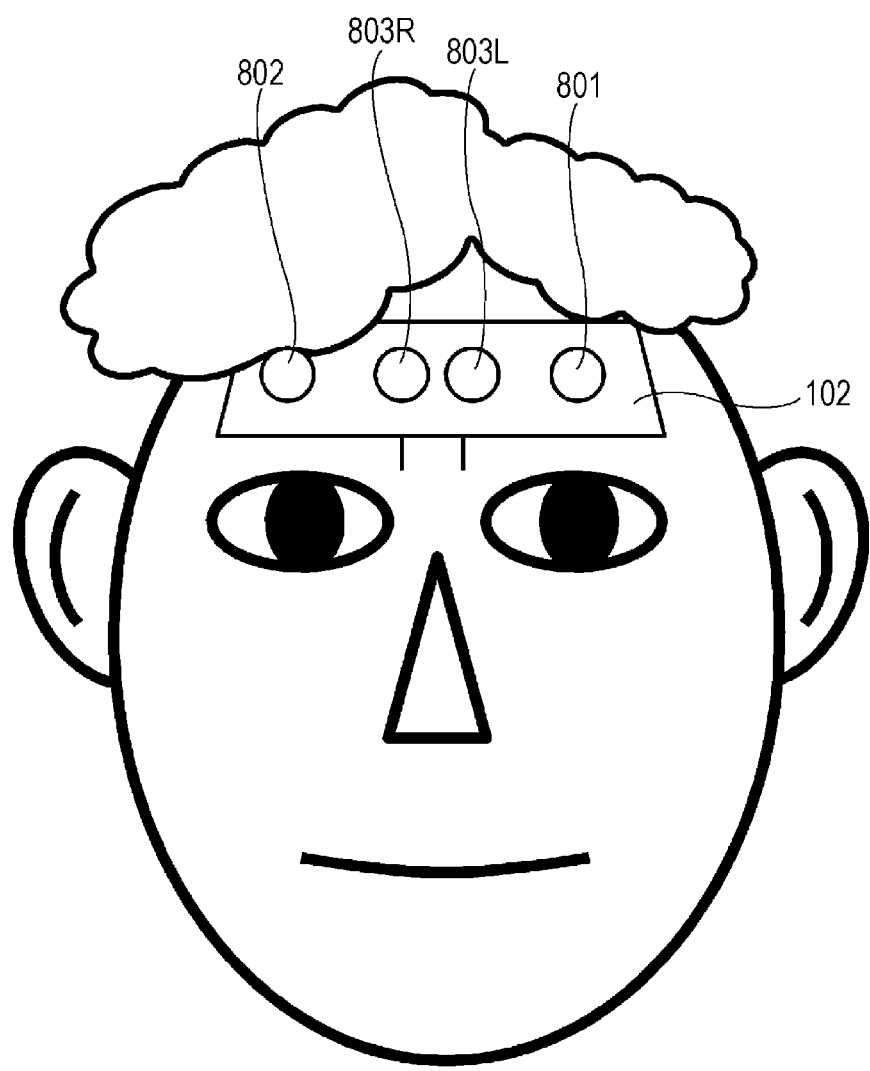

[Fig. 14]
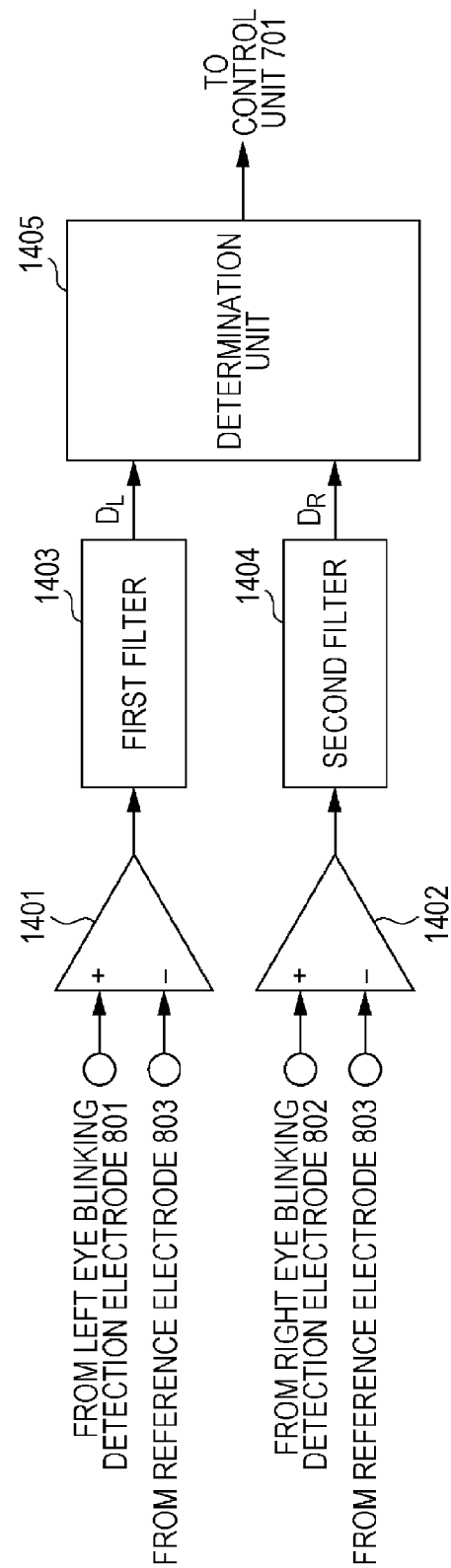

[Fig. 15]
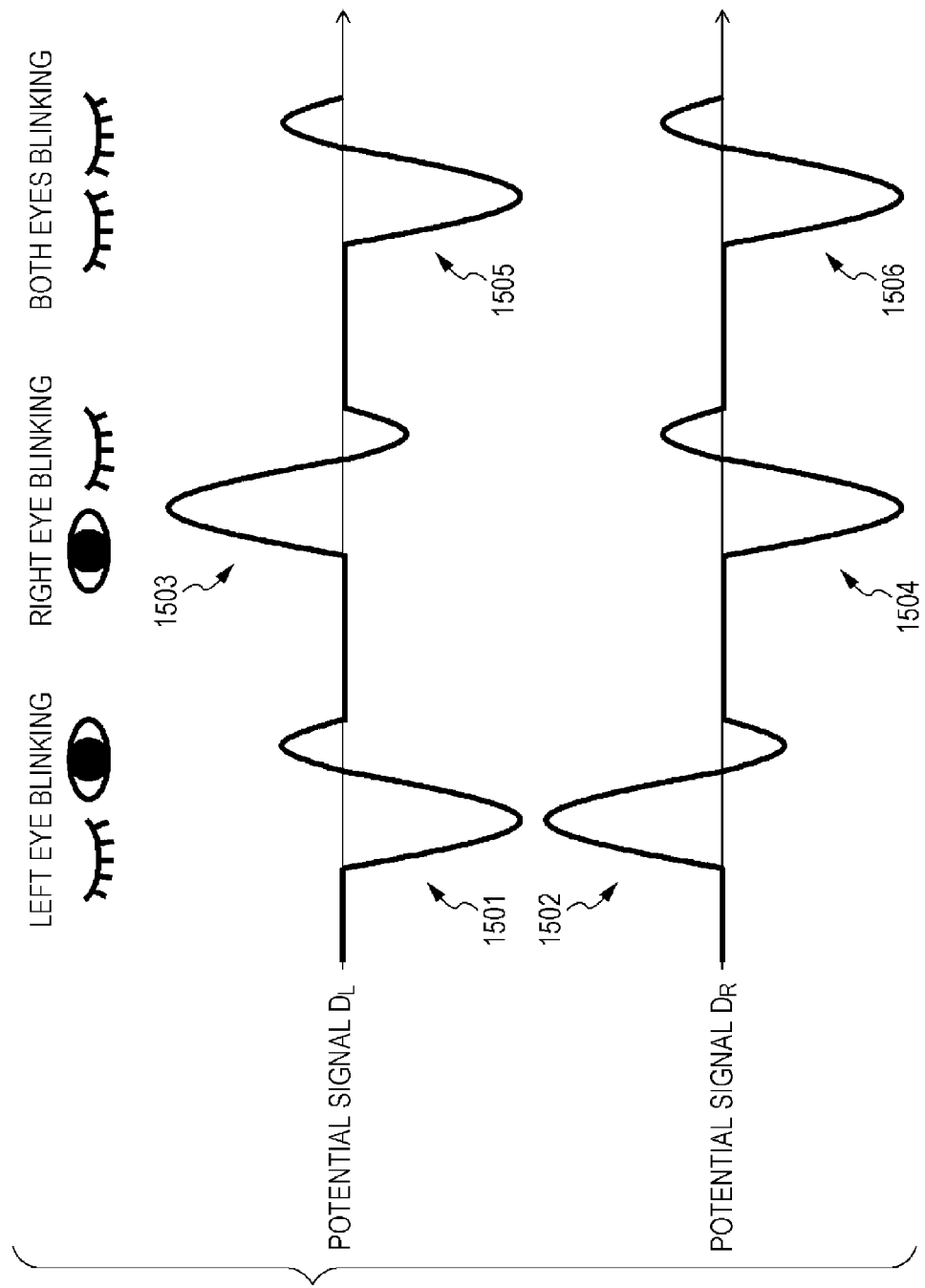

[Fig. 16]
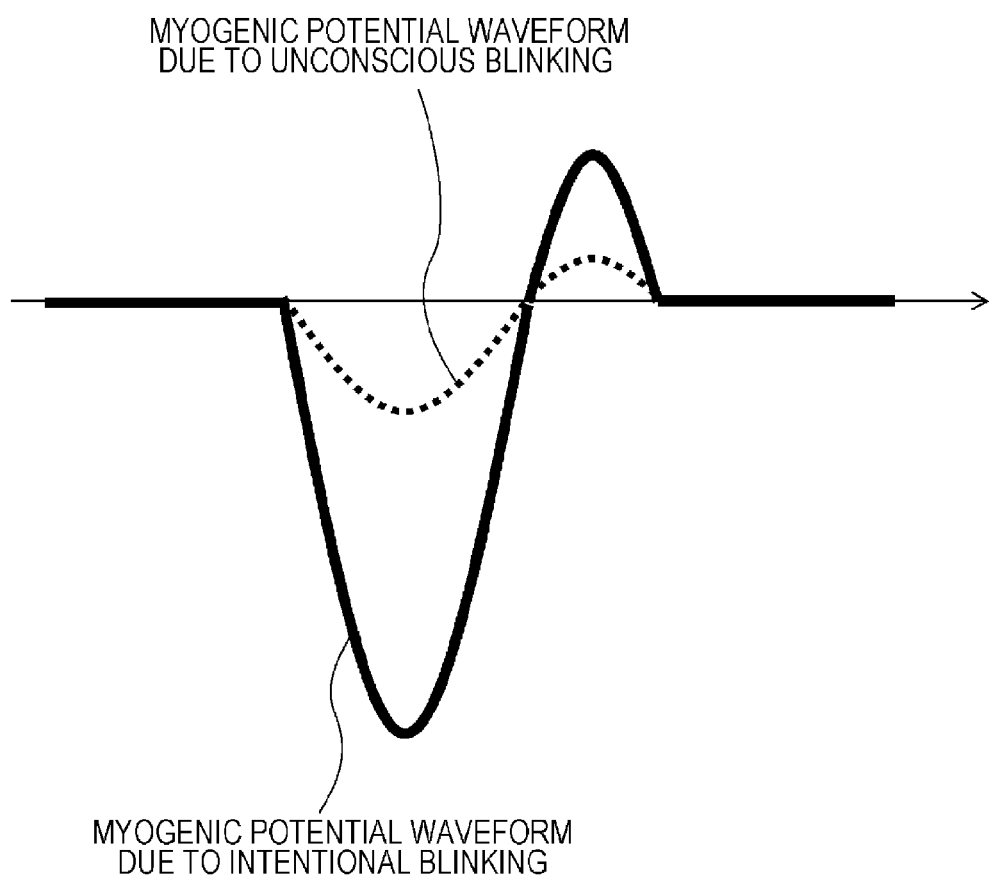

[Fig. 17]
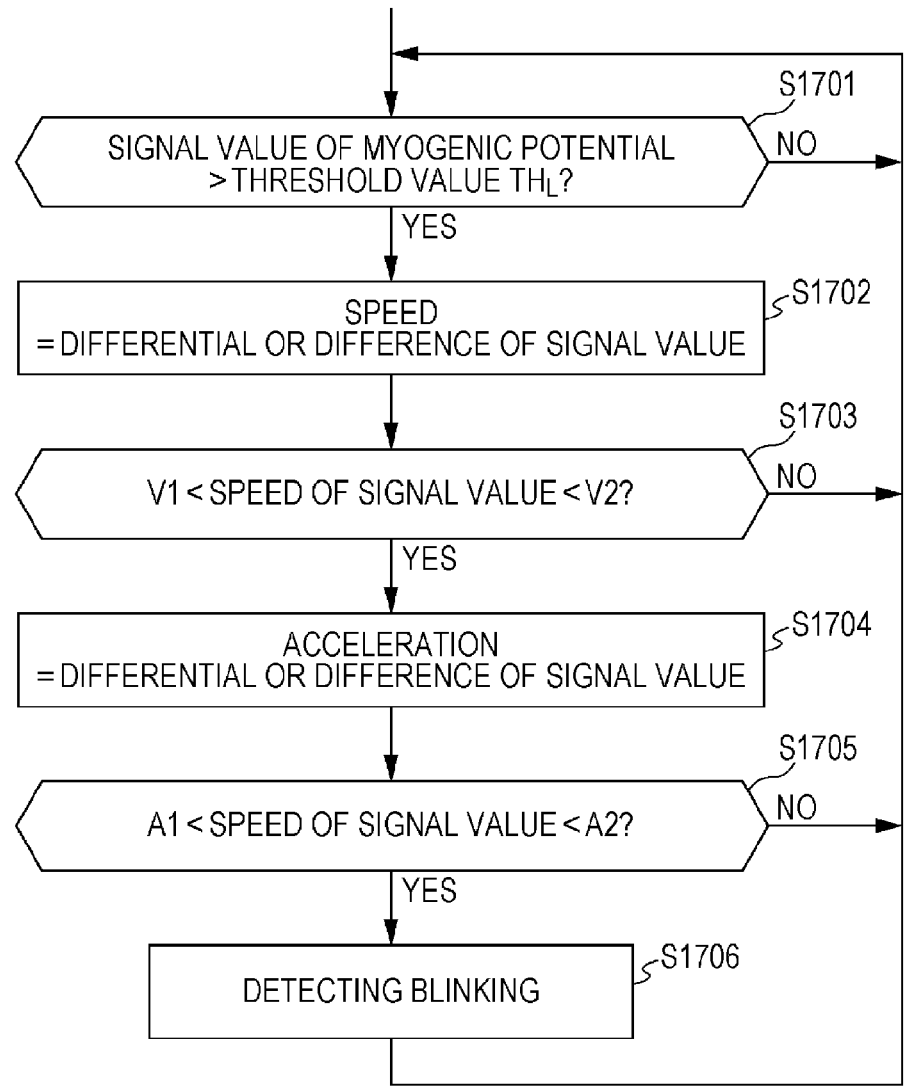

[Fig. 18]
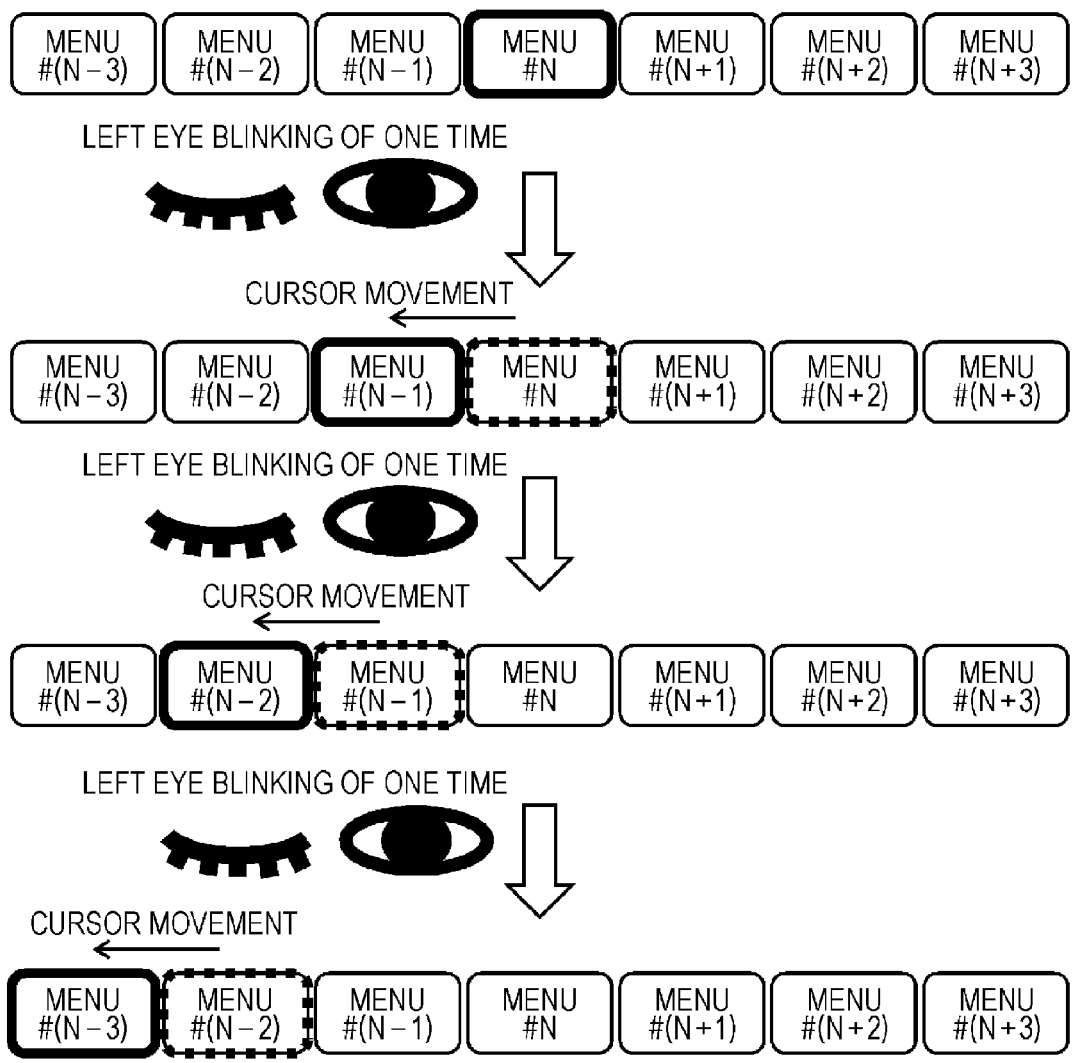

[Fig. 19]
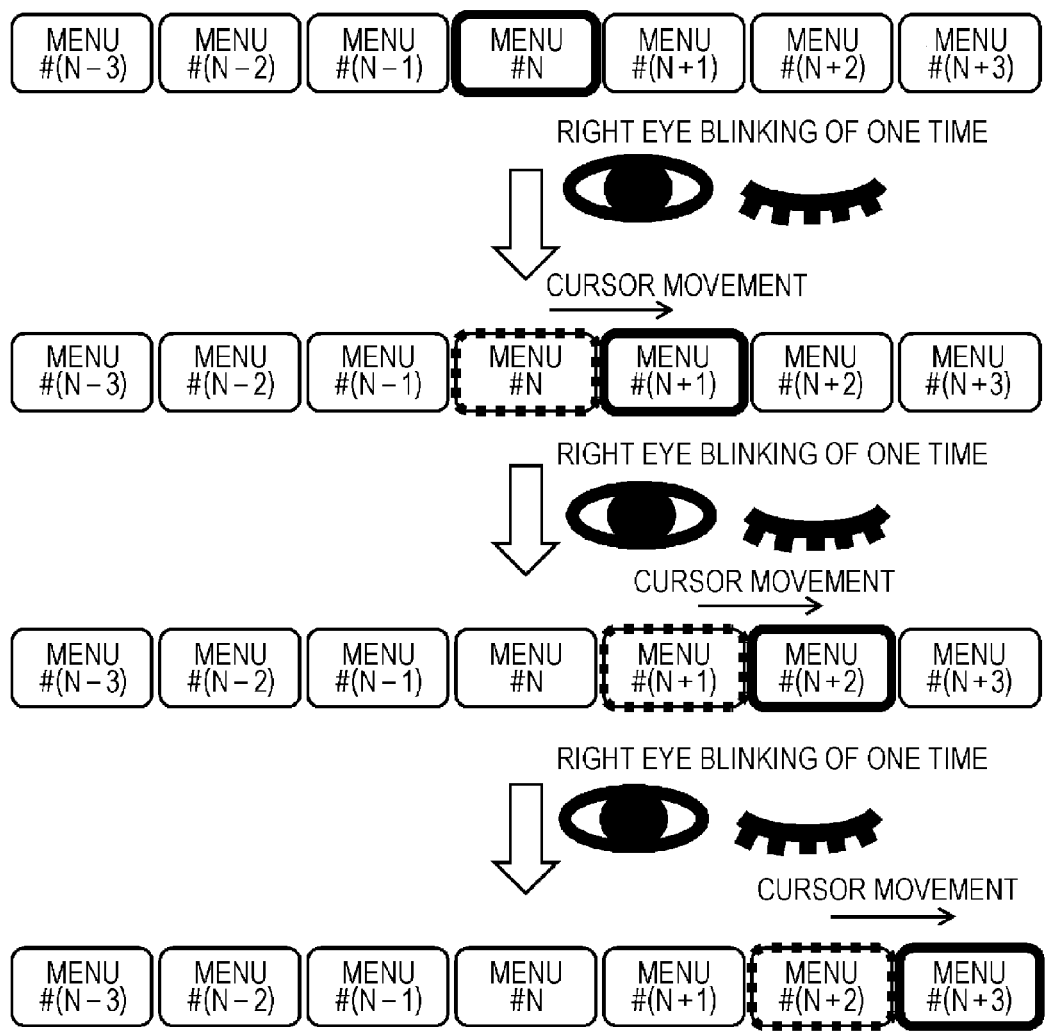

[Fig. 20]
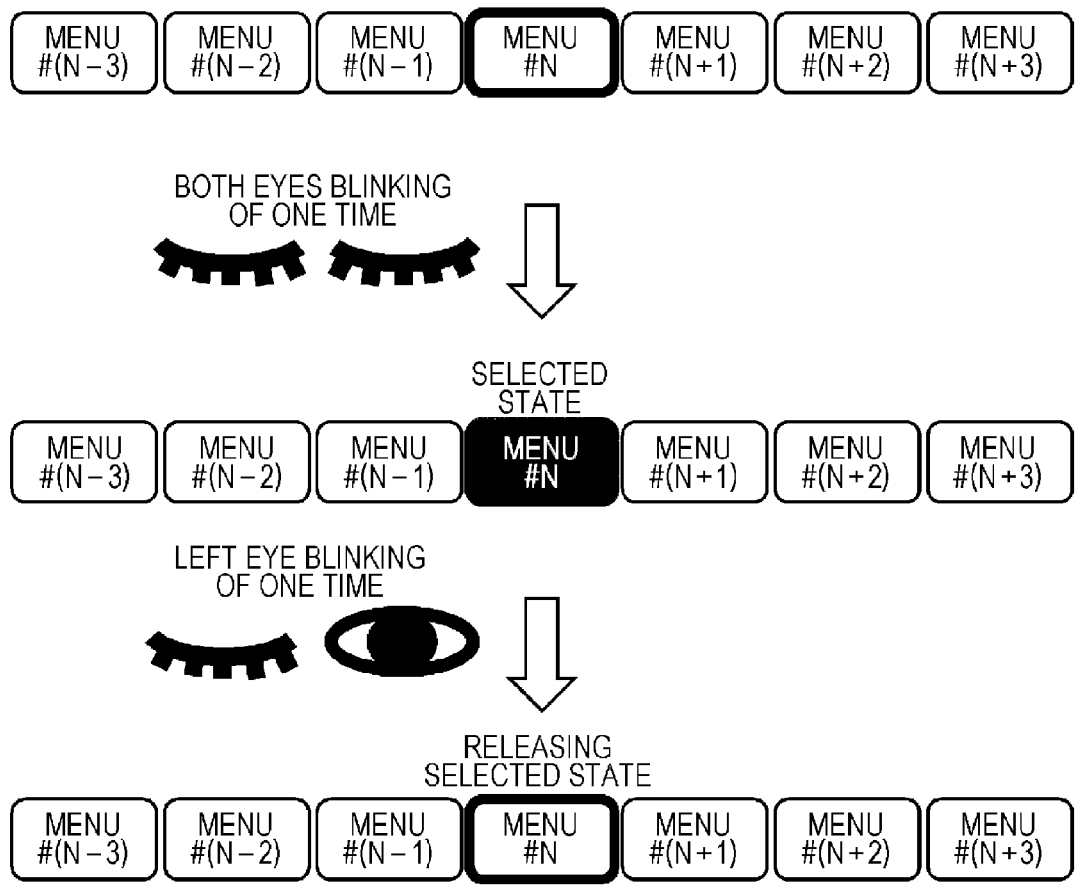

[Fig. 21]
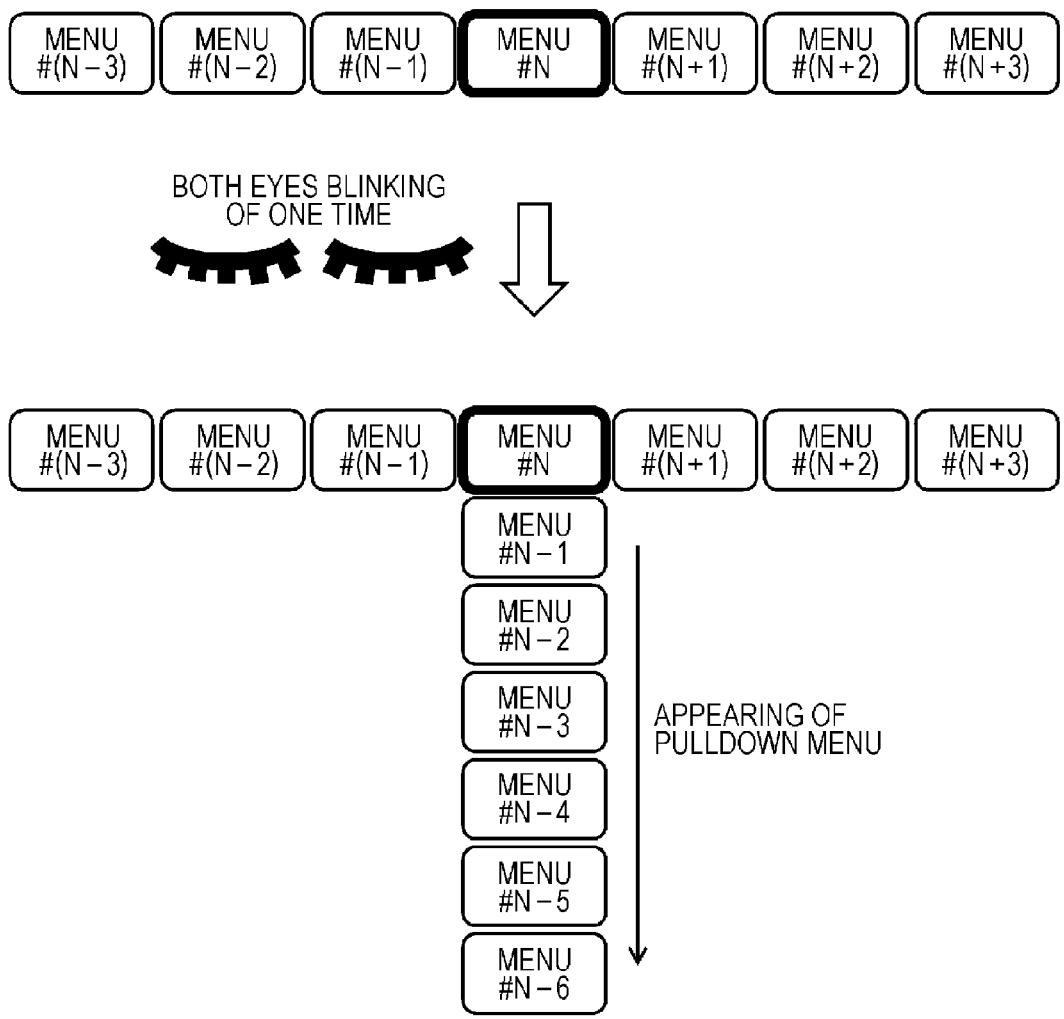

[Fig. 22]
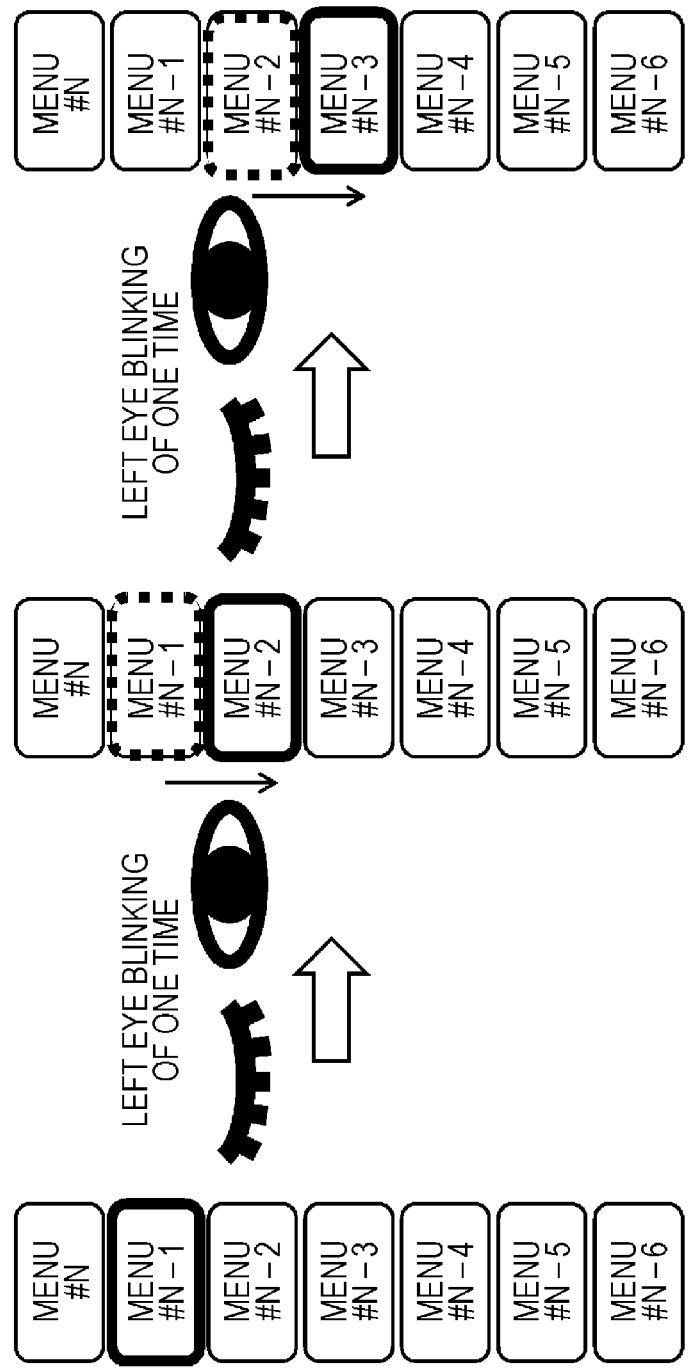

[Fig. 23]
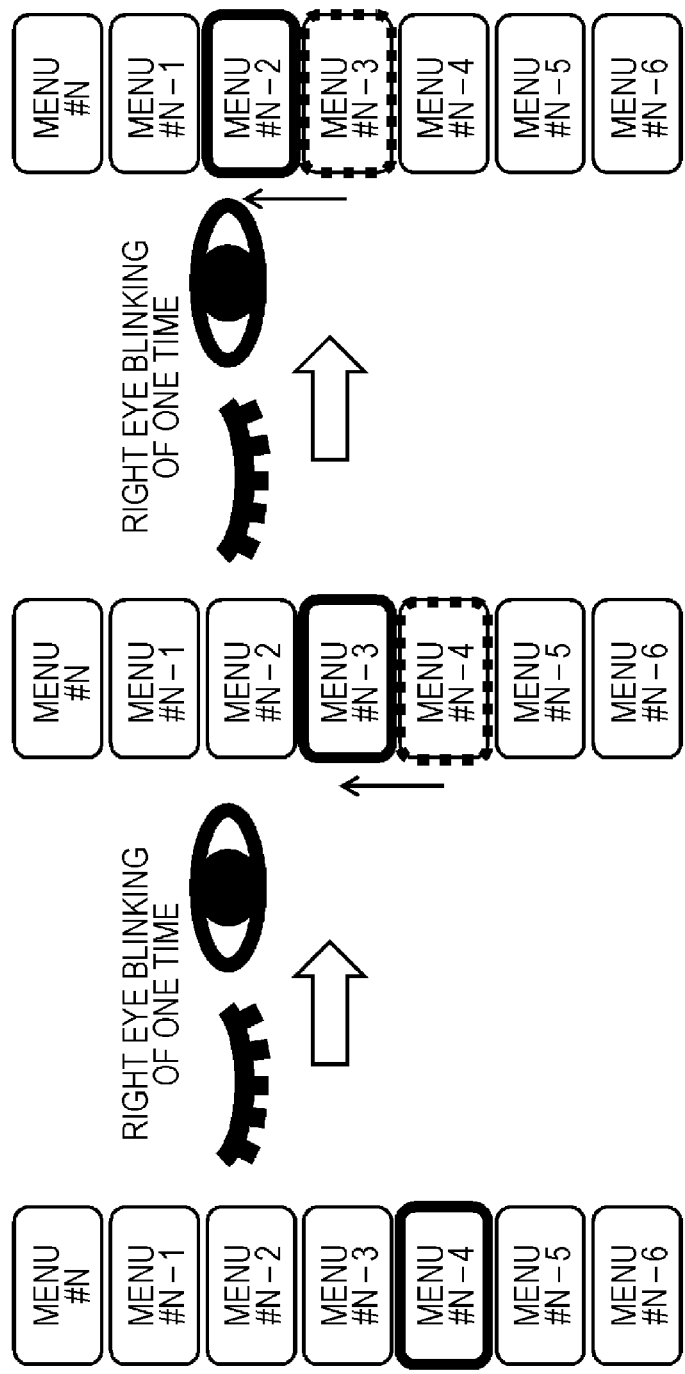

[Fig. 24]
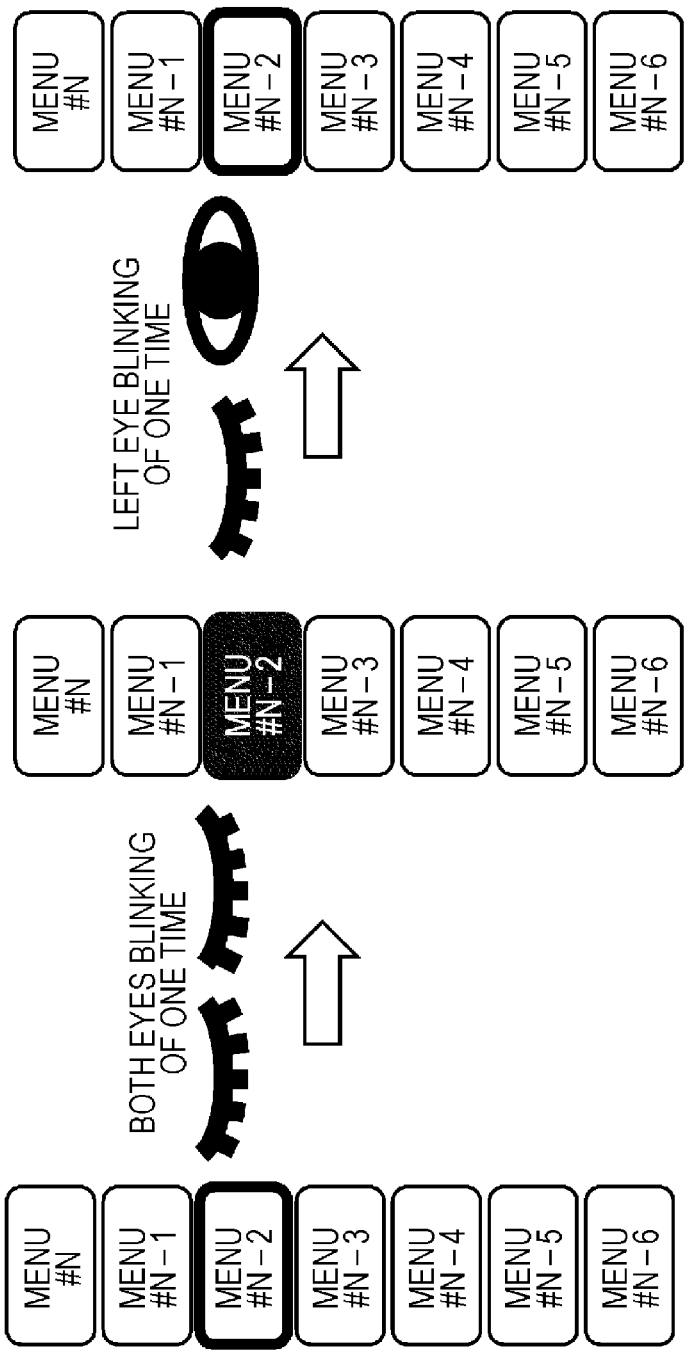

[Fig. 25]
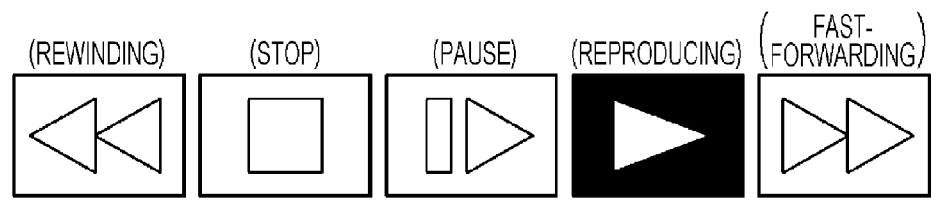
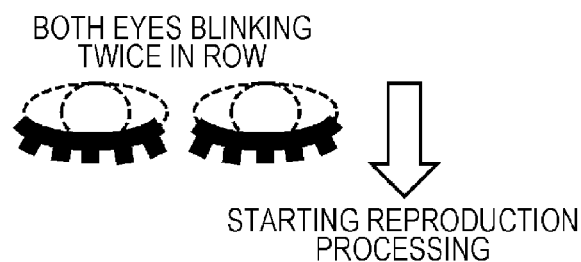
[Fig. 26]
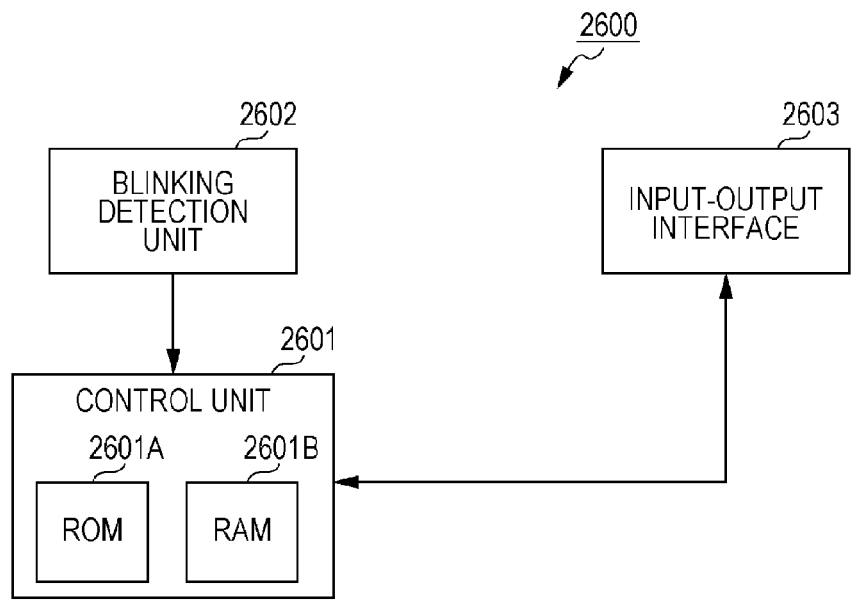

IMAGE DISPLAY DEVICE AND INFORMATION INPUT DEVICE

CROSS-REFERENCE TO RELATED APPLICATION

The present application is a national phase entry under 35 U.S.C. §371 of International Application No. PCT/JP2013/005380 filed Sep. 11, 2013, published on May 8, 2014 as WO 2014/068832 A1, which claims priority from Japanese Patent Application No. JP 2012-243065 filed in the Japanese Patent Office on Nov. 2, 2012.

TECHNICAL FIELD

A technology which is disclosed in the specification relates to an image display device which is used when a user wears the device at a head portion, and sees and hears an image, and an information input device by which a user performs an input operation by wearing the device. In particular, the technology relates to the image display device and the information input device which are operated based on eye movements of a user wearing the devices.

BACKGROUND ART

A head-mounted image display device which is used when seeing and hearing an image by wearing the device at a head portion, that is, a head-mounted display has been known. The head-mounted image display device includes, for example, image display units for respective left and right eye, and is configured so as to control sight and hearing by using a headphone together. In addition, the head-mounted image display device is able to project images which are different in the left and right eyes, and to provide a 3D image when displaying an image with parallax in the left and right eyes.

It is also possible to classify the head-mounted image display device into a light shielding type and a transmission type. A head-mounted image display device of a light shielding type is configured so as to directly cover user's eyes when being mounted on a head portion, and a level of concentration of a user increases when seeing and hearing an image. On the other hand, in a case of a head-mounted image display device of a transmission type, since a user is able to see an outside view (that is, see through) beyond an image while displaying the image by mounting the device at a head portion, it is possible for the user to avoid a danger such as a collision with an obstacle when using the device outdoors, or while walking.

A lot of head-mounted image display devices are used for enjoying contents by being connected to an AV reproducing apparatus such as a DVD player, or a blue-ray disk (BD) player (for example, refer to PTL 1). Here, when seeing and hearing an image, it is necessary to instruct a user to turn volume up or down of a headphone, a start, a stop, fast forwarding, fast returning, or the like of reproducing contents with respect to a device.

For example, a head-mounted image display device to which a controller including a menu button for displaying a menu or deciding a selected item, an up button, and a down button for moving a targeted menu item, a volume dial for adjusting volume, and the like is connected has been proposed (for example, refer to PTL 2). However, a user wearing the head-mounted image display device is apt to perform an erroneous operation by fumbling for the controller, and treating the controller. In particular, in a case of the head-mounted image display device of light shielding type, since a user is almost in a blindfolded state, it is difficult to operate the controller.

Since the head-mounted image display device is in close contact with a user while being used, it is easy to obtain biological information of the user. By paying attention to the point, a try of performing an User Interface (UI) operation based on biological information which is measured from a user wearing the device has been performed. For example, it is possible to relatively easily obtain information on a movement of eyes of a user by making use of a device configuration such as a close contact with a head portion.

In the technical field, a method has been known in which eyes are photographed using a camera, and a movement of an eyeball, or blinking is caught using image processing. For example, a goggles type display which includes a line of sight input device performing a screen operation by detecting a reflection from an eyeball using infrared light, and detecting a position of a line of sight, or blinking, and performs a video reproducing operation, or an input operation of a personal computer without using a hand has been proposed (for example, refer to PTL 3).

However, the line of sight input device should be provided so as not to be an obstruction in a field of vision in the head-mounted image display device, and there is much limitation in a design and manufacturing. In addition, in particular, when it is a light shielding-type image display device, since an eyeball is photographed in an almost dark place, it is necessary to use a high sensitive camera when inputting a line of sight, and to perform high-definition image processing, accordingly, it results in an increase in cost of the device.

In addition, a head-mounted display in which a line of sight is detected by measuring an eye potential which is generated by a positive charge of a cornea and a negative charge of a retina using a plurality of electrodes which are attached to the periphery of eyes, that is, using Electro-Oculography (EGG), or the like has been proposed (for example, refer to PTL 4). However, an eye potential associated with a movement of an eyeball, a myogenic potential associated with blinking, and brainwaves are mixed in a potential difference signal which is input from the electrode, and it is necessary to treat them separately (for example, extracting only potential difference signal which is caused by blinking). In the head-mounted display, a rapid sacchadic movement of an eyeball at the time of moving of a position of a line of sight of a user is detected from an eye potential signal, and a steep change in a voltage which occurs due to blinking is eliminated.

CITATION LIST

Patent Literature

[PTL 1]
Japanese Unexamined Patent Application Publication No. 2005-86328
[PTL 2]
Japanese Unexamined Patent Application Publication No. 2001-133724
[PTL 3]
Japanese Unexamined Patent Application Publication No. 2000-23065
[PTL 4]
Japanese Unexamined Patent Application Publication No. 2011-125693
[PTL 5]
Japanese Unexamined Patent Application Publication No. 2012-138654

SUMMARY

Technical Problem

It is desirable to provide an excellent image display device and an information input device which are used by being mounted on a head portion of a user, and are preferably operated based on a movement of eyes of the user.

Solution to Problem

In view of the above, the embodiments of the present technology are provided. According to an illustrative embodiment, an information processing device includes at least one electrode configured to generate at least one signal related to eye blinking of a subject; and a processing circuit configured to receive the at least one signal and detect eye blinking of the subject based on the at least one signal.

Advantageous Effects of Invention

According to the technology which is disclosed in the present specification, it is possible to provide an excellent image display device and an information input device which are used by being mounted on a user's head portion, and are preferably operated based on movements of eyes of the user.

The image display device and the information input device to which the technology disclosed in the specification is applied are able to accurately detect blinking of a user based on a myogenic potential signal which is detected in the vicinity of the left and right eyes of a user wearing the device, and to perform a UI operation in which a hand is not used based on a combination of blinking on the left and right eyes.

Still other objectives, characteristics, and advantages of the technology which are disclosed in the specification will be clarified according to further detailed descriptions based on embodiments which will be described later, or accompanying drawings.

BRIEF DESCRIPTION OF DRAWINGS

FIG. 1 is a perspective view which illustrates an image display device according to an embodiment of the present technology is viewed from the front.

FIG. 2 is a perspective view which illustrates the image display device according to the embodiment of the present technology is viewed from the rear side.

FIG. 3 is a side view of the image display device according to the embodiment of the present technology.

FIG. 4 is diagram which illustrates a configuration example of a mounted sensor which is equipped in a forehead contact unit.

FIG. 5 is a diagram which illustrates a height adjusting mechanism which is equipped in the forehead contact unit.

FIG. 6 is a diagram which illustrates a height adjusting mechanism which is equipped in the forehead contact unit.

FIG. 7 is a diagram which illustrates an inner configuration example of an image display device to which the technology disclosed in the present specification is applied.

FIG. 8 is a diagram (front view) which illustrates an example in which a myogenic potential sensor for detecting blinking is arranged at the forehead contact unit.

FIG. 9 is a diagram (top view) which illustrates an example in which the myogenic potential sensor for detecting blinking is arranged at the forehead contact unit.

FIG. 10 is a diagram describing an eye potential signal which is input to blinking detection electrodes when eyes of a user move in the horizontal direction.

FIG. 11 is a diagram describing the eye potential signal which is input to a reference electrode when both eyes of the user move to the right side.

FIG. 12 is a diagram describing the eye potential signal which is input to the reference electrode when both eyes of the user move to the left side.

FIG. 13 is a diagram (front view) which illustrates another example in which the myogenic potential sensor for detecting blinking is arranged at the forehead contact unit.

FIG. 14 is a diagram which schematically illustrates a circuit configuration in which an output signal of the myogenic potential sensor which is illustrated in FIGS. 8 and 9 is processed.

FIG. 15 is a timing chart which illustrates a potential signal obtained from the blinking detection electrode for left eye, and the blinking detection electrode for right eye, respectively.

FIG. 16 is a timing chart in which a myogenic potential level when blinking is made intentionally, and a myogenic potential level when blinking is made unintentionally are overlappingly illustrated.

FIG. 17 is a timing chart in which a myogenic potential level when blinking is made intentionally, and a myogenic potential level when blinking is made unintentionally are overlappingly illustrated.

FIG. 18 is a diagram which illustrates an UI operation example in which blinking of a user is used (diagram which illustrates state in which cursor position on menu bar is moved to left direction one by one according to one blinking of left eye).

FIG. 19 is a diagram which illustrates an UI operation example in which blinking of the user is used (diagram which illustrates state in which cursor position on menu bar is moved to right direction one by one according to one blinking of right eye).

FIG. 20 is a diagram which illustrates an UI operation example in which blinking of the user is used (diagram which illustrates state in which current cursor position on menu bar is selected according to simultaneous blinking of both eyes).

FIG. 21 is a diagram which illustrates an UI operation example in which blinking of the user is used (diagram which illustrates state in which list of menus is displayed by being pulled down from menu selected according to simultaneous blinking of both eyes).

FIG. 22 is a diagram which illustrates an UI operation example in which blinking of the user is used (diagram which illustrates state in which cursor position is moved up and down on pulldown menu according to blinking of left eye and right eye).

FIG. 23 is a diagram which illustrates an UI operation example in which blinking of the user is used (diagram which illustrates state in which cursor position is moved up and down on pulldown menu according to blinking of left eye and right eye).

FIG. 24 is a diagram which illustrates an UI operation example in which blinking of the user is used (diagram which illustrates state in which menu item is selected on pulldown menu according to simultaneous blinking of left eye and right eye).

FIG. 25 is a diagram which illustrates an UI operation example in which blinking of the user is used (diagram which illustrates state in which selection of blinking in both eyes is determined twice in a row).

FIG. 26 is a diagram which illustrates an inner configuration example of an information input device to which the technology disclosed in the specification is applied.

DESCRIPTION OF EMBODIMENTS

Hereinafter, embodiments of the technology which is disclosed in the specification will be described in detail with reference to drawings.

[A. Device Configuration]

FIG. 1 illustrates a state in which an image display device according to an embodiment of the present technology is viewed from the front. In addition, FIG. 2 illustrates a state in which an image display device according to the embodiment of the present technology is viewed from the rear side. The illustrated image display device is a head-mounted structure body which is similar to a hat shape, and it is possible to mount the device by reducing a burden of a user by spreading a load of the device on the whole head portion even when a heavy load is concentrated in the front portion of a main body.

In addition, FIG. 3 illustrates a state in which the image display device according to the embodiment of the present technology is viewed from the side. The image display device according to the embodiment is configured by a main body unit 101 including most of components which includes a display system, a forehead contact unit 102 which protrudes from the top face of the main body unit 101, a head band which is branched off to the upper band 104 and the lower band 105 on the rear side, and a horizontal headphone. A display unit or a circuit board is accommodated in the main body unit 101. In addition, a nose contact unit 103 imitating dorsum of nose is provided at the lower part of the main body unit 101.

When a user wearing the image display device at an appropriate position of a head portion, the forehead contact unit 102 comes into contact with a forehead of the user, and the upper band 104 and the lower band 105 of the head band come into contact with the rear side of the head portion. That is, a head-mounted display is mounted on the head portion of the user when being supported by three points of the forehead contact unit 102, the upper band 104, and the lower band 105. It is possible to support the main body of the image display device so as not to rotate on the head portion of the user by tightening the head band in a state in which the forehead of the user comes into contact with the forehead contact unit 102.

The forehead contact unit 102 is equipped with a mounting sensor which detects that the image display device is mounted on the user in association with the movement of the device coming into contact with a head portion of a forehead, when the image display device is mounted on the head portion of the user. FIG. 4 illustrates a configuration example of the mounting sensor which is equipped in the forehead contact unit 102. In the illustrated example, the forehead contact unit 102 is rotatably supported by an outer housing of the image display device by a rotation shaft 142. The forehead contact unit 102 is pushed out to the rear side of the image display device, that is, a non-wearing position facing the forehead side of the user who wears the device due to a restoring force of a spring 144 when not wearing the device. In addition, when wearing the device, the forehead contact unit returns to the mounting position on the front side by being pressed when the forehead of the user comes into contact therewith. In addition, an arm 143 which protrudes to the front side is attached to the rotation shaft 142. When wearing the device, the forehead contact unit 102 rotates approximately by 10 degrees around the rotation shaft 142. Accordingly, when a user wears the device, and the forehead contact unit 102 returns to the front side by being pressed, the arm 143 is interlocked, and a tact switch 141 is operated at a tip end portion thereof. It is possible to detect mounting of the image display device on the head portion of the user from the operation of the tact switch 141.

In addition, the forehead contact unit 102 is equipped with a height adjusting mechanism. FIG. 5 illustrates a state in which the height of the forehead contact unit 102 is switched due to an operation of the height adjusting mechanism. In the figure, the forehead contact unit 102 which is set to the lower position is denoted by a solid line, and the forehead contact unit 102 which is set to the upper position is denoted by a dotted line. As illustrated, when adjusting the height of the forehead contact unit 102 to the upper position from the lower position, it is possible to widen a range corresponding to an individual difference in size of a head of a user.

The adjusting of the height in the forehead contact unit 102 is not limited to a specified mechanism. For example, it is possible to easily adjust the height by an operation of reattaching the forehead contact unit 102 by configuring the forehead contact unit 102 so as to be detachable, and by providing attaching positions in the lower position and the upper position. FIG. 6 illustrates a cross-sectional view of the forehead contact unit 102 which is attached to the lower position on the left, and illustrates a cross-sectional view of the forehead contact unit 102 which is attached to the upper position on the right, respectively.

The image display device which is illustrated in FIGS. 1 to 6 is a light shielding type which is configured so as to directly cover eyes of a user wearing thereof, and a level of concentration of the user increases when seeing and hearing an image, however, the user is in a blindfold state. In the image display device, the forehead contact unit 102 typically comes into close contact with a face of the user in a state of being mounted on the user's head portion. There is an individual difference in a position or the height of a forehead in a face, however, as illustrated in FIG. 6, adherence is secured by adjusting the height. Accordingly, it is possible to arrange an electrode for detecting a potential from the head portion of the user in the forehead contact unit 102, or the nose contact unit 103.

FIG. 7 illustrates an inner configuration example of an image display device 700 to which the technology which is disclosed in the specification is applied. Hereinafter, each component will be described.

A control unit 701 includes a Read Only Memory (ROM) 701A, or a Random Access Memory (RAM) 701B. A program code which is executed in the control unit 701, or various data items are stored in the ROM 701A. The control unit 701 performs an overall control of the entire operation of the device 700, including a display control of an image, by executing a program which is loaded in the RAM 701B. As the program, or data which is stored in the RAM 701A, there is a display control program of an image, a processing program of environment information which is obtained in an environment information obtaining unit 704, a processing program of state information which is obtained in a state information obtaining unit 705, identification information which is unique to the device 700, or the like.

An input operation unit 702 includes one or more operators with which a user performs an input operation such as a key, a button, or a switch, receives an instruction of a user through the operator, and outputs the instruction to a control unit 701. In addition, the input operation unit 702 similarly receives the instruction of the user which is formed by a remote control command which is received in a remote control reception unit 703, and outputs thereof to the control unit 701. However, for a user who is wearing the device 700, the operation of the input operation unit 702 or a remote controller (not shown) becomes a fumbling operation almost in a blindfolded state.

The environment information obtaining unit 704 obtains environment information relating to a peripheral environment of the device 700, and outputs thereof to the control unit 701. The environment information obtaining unit 704 obtains, for example, an environmental light intensity, a sound intensity, a position or place, a temperature, weather, a time, an image in the periphery, or the like, as the environment information. In addition, the environment information obtaining unit 704 may include various environment sensors such as a light amount sensor, a microphone, a Global Positioning System (GPS) sensor, a humidity sensor, a temperature sensor, a clock, an image sensor (camera), a radiation sensor, and the like (any of those is not shown in FIG. 7) in order to obtain the environment information. Alternatively, the device 700 may be configured so as to obtain environment information by the environment information obtaining unit 704 from an external device (not shown) which includes an environment sensor, without including the environment sensor for itself.

The state information obtaining unit 705 obtains state information relating to a state of a user who uses the device 700, and outputs thereof to the control unit 701. The state information obtaining unit 705 obtains, for example, a work state (whether or not user wearing device) of a user, a behavior state of the user (posture of head portion of user while wearing device, state of movement such as walking, opening and shutting state of eyelids), a mental state (degree of excitement while observing inner image such as immersing, concentration, or the like, degree of awakening, feeling, emotion, or the like) and a physical state. In addition, the state information obtaining unit 705 may include various state sensors such as a mounting sensor which is formed by a mechanic switch, or the like (refer to FIG. 4), a gyro sensor, an acceleration sensor, a speed sensor, a pressure sensor, a body temperature sensor, a sweat sensor, a myogenic potential sensor, an eye potential sensor, a brainwaves sensor (any of those is not shown in FIG. 7) in order to obtain the state information from a user.

According to the embodiment, the state information obtaining unit 705 includes a myogenic potential sensor for measuring a myogenic potential in the vicinity of eyes of a user who is wearing the device 700. The control unit 701 is assumed to obtain operation information with respect to the device 700 by detecting blinking of a user based on an obtained myogenic potential, however, detailed descriptions thereof will be made later.

The communication unit 706 performs communication processing with another device, modulation/demodulation of a communication signal, and encoding/decoding processing. For example, the communication unit 706 receives an image signal for displaying and outputting from an external device (not shown) as an image source. An inner image, or an outer image which is received in the communication unit 706, and is performed with demodulation and decoding processing, or the other received data is supplied to the control unit 701. In addition, the control unit 701 sends out transmission data to be sent to the external device from the communication unit 706.

A configuration of the communication unit 706 is arbitrary. For example, it is possible to configure the communication unit 706 according to a communication standard which is used in transmitting and receiving operation with the external device as a communication partner. The communication standard may be either a wired type or a wireless type. As the communication standard referred to here, there is a Mobile High-definition Link (MHL), a Universal Serial Bus (UBS), a High Definition Multimedia Interface (HDMI), a Bluetooth (registered trade mark) communication, an infrared communication, or the like.

An image processing unit 707 further performs signal processing such as an image quality correction with respect to the image signal which is output from the control unit 701, and a conversion into a resolution which fits a screen of a display panel 709 is performed. In addition, a display driving unit 708 sequentially selects pixels in the display panel 709 in each row, line sequentially scans thereof, and supplies a pixel signal based on the image signal in which the signal processing is performed.

The display panel 709 is configured by a micro display such as, for example, an organic EL element, or a liquid crystal display. A virtual image optical unit 710 causes a user to observe a display image of the display panel 709 as an enlarged virtual image by largely projecting the image.

The image display device 700 is the light shielding type which is configured so as to directly cover eyes of a user, and in which an input operation with respect to the input operation unit 702, or a remote controller becomes difficult since the user is in a blindfold state while wearing the device. Therefore, according to the embodiment, the state information obtaining unit 705 performs an input operation based on blinking of the left and right eyes which is obtained as a user state.

As another method of performing an input operation using an eye movement of a user, a head-mounted display which performs an input operation in the direction of a line of sight, not the blinking, or a wearable device has been known (for example, refer to PTLs 3 and 4). However, it is difficult to accurately specify the direction of line of sight, and when a plurality of menu buttons are displayed by being in close contact with each other, a case is also assumed in which a neighboring menu button is pressed by mistake. In contrast to this, the blinking is a discrete output for only determining whether or not eyelids are closed, and is considered to be able to clearly interpret an instruction of a user.

An UI operation using the blinking is simple, and easy to use for a user. The user is able to perform three inputs of blinking only in the left eye, blinking only in the right eye, and simultaneous blinking in both eyes. For example, it is possible to allocate an UI operation such as a cursor movement in the left direction for the blinking only in the left eye, and a UI operation such as a cursor movement in the right direction for the blinking only in the right eye, respectively. The UI operation in which the cursor moves to the left in the left eye blinking, and the cursor moves to the right in the right eye blinking is easy for a user to intuitively understand thereof.

[B. Detection of Blinking of User]

A method of catching a movement of an eyeball or blinking by performing image processing with respect to a photographed image or the like of a camera has been widely known in the field of technology. However, a line of sight input device should be provided in the image display device which is mounted on a head portion so as not to disturb a field of vision, accordingly, there is a lot of limitation in designing and manufacturing.

Therefore, according to the embodiment, blinking of a user is detected based on an obtained myogenic potential by providing a myogenic sensor which measures the myogenic potential in the vicinity of eyes of the user who is wearing the device. Since it is possible to determined whether or not the blinking is made by comparing the detected myogenic potential with a threshold value, determination on the blinking is done with simple processing when compared to image processing of a photographed image of a camera, or detecting of the direction of line of sight.

In order to detect the myogenic potential which is caused by the blinking of eyes, it is necessary to combine a detection electrode for catching a change in the myogenic potential, and a reference electrode for obtaining a reference myogenic potential. In addition, since adherence between the forehead contact unit 102 and a face of a user is secured in the configuration of the image display device which is illustrated in FIGS. 1 to 6, according to the embodiment, the detection electrode and the reference electrode are arranged in the forehead contact unit 102. Naturally, places at which the electrodes are arranged may be appropriately moved to other places than the forehead contact unit 102 according to a change in a device configuration.

Examples in which the myogenic sensor which is formed by blinking detection electrode is arranged in the forehead contact unit 102 are illustrated in FIGS. 8 and 9. However, FIG. 8 is a diagram which illustrates a state viewed from the front of a user's face, and FIG. 9 is a diagram which illustrates a state viewed from head portion information of the user. In the illustrated examples, a blinking detection electrode for the left eye 801 comes into contact with the left eye of the user wearing the device approximately right thereabove, and a blinking detection electrode for the right eye 802 comes into contact with the right eye of the user wearing the device approximately right therebelow. In addition, in the examples illustrated in FIGS. 8 and 9, a reference electrode 803 which is shared by each of the detection electrodes 801 and 802 is arranged near a center between the detection electrodes 801 and 802.

As electrode materials of the detection electrodes 801 and 802, and the reference electrode 803, for example, the followings can be used.

(1) Conductive gel electrode (disposable electrode for bioelectric measurement, electrode for electric stimulation, or the like)

(2) Dry electrode (conductive cloth in which conductive thread is knitted, cloth which is formed by depositing or applying conductive material on insulating cloth, or the like)

(3) Non-contact type capacity coupling electrode

Here, as illustrated in FIGS. 8 and 9, a component of an eye potential which is generated by a movement of an eyeball is input to the electrode which comes into contact with a human forehead, in addition to a component of a myogenic potential which is generated by a movement of muscles performing blinking. It is known that the eye potential is generated by a positive charge of a cornea and a negative charge of a retina, the positive charge occurs when an iris comes closer, and in contrast to this, the negative charge occurs when the iris goes away. Basically, the movement of the eyeball is a movement on the left and right of the iris, that is, the horizontal direction. Even when the iris in the left eye moves, since a distance between the detection electrode 801 which is arranged approximately right above the left eye and the iris is hardly changed, a potential signal which is input to the detection electrode 801 is hardly influenced by a change in an eye potential which is caused by a movement of the left eyeball. Similarly, even when the iris in the right eye moves, since a distance between the detection electrode 802 which is arranged approximately right above the right eye and the iris is hardly changed, a potential signal which is input to the detection electrode 802 is hardly influenced by a change in an eye potential which is caused by a movement of the right eyeball. As illustrated in FIG. 10, differences in the distances L1, L2, and L3 to the detection electrode 801, or 802 in each position P1, P2, and P3 of the iris are small, and accordingly, an influence by the eye potential can be approximately the same. In addition, even when the detection electrodes 801 and 802 are arranged approximately right below the eye, not approximately right above the eye, similarly, an influence by a change in the eye potential which is caused by the movement of the eyeball is hardly received.

On the other hand, the reference electrode 803 is arranged at a place in which a distance from the left eye and a distance from the right eye is approximately the same. As illustrated in FIG. 11, since a negative potential which occurs when the iris in the right eye goes away, and a positive potential which occurs when the iris in the left eye comes closer are offset when both eyes of the user turns to the right, there is almost no influence of a change in the eye potential which is caused by the movement of both eyeballs. Similarly, as illustrated in FIG. 12, since a positive potential which occurs when the iris in the right eye comes closer, and a negative potential which occurs when the iris in the left eye goes away are offset when the user turns to the left, there is almost no influence of a change in the eye potential which is caused by the movement of both eyeballs. When the reference electrode 803 is arranged approximately in a center of a face (forehead), even when a line of sight of the user is present at any position, since the other iris goes away when any one of the left and right irises comes closer, the change in the eyeball potential is offset in the left and right eyes.

In brief, as illustrated in FIGS. 8 and 9, by adopting a configuration of a myogenic potential sensor in which the left eye blinking detection electrode 801 is arranged approximately right above the left eye, the right eye blinking detection electrode 802 is arranged approximately right above the right eye, and the reference electrode 803 is arranged near the center of each detection electrodes 801 and 802, it is possible to detect blinking by suppressing the influence by the eye potential. In addition, when it is possible to maintain a positional relationship in each electrode 801, 802, and 803 which is described above, the myogenic potential sensor may be arranged at a place excluding the forehead contact unit 102.

FIG. 13 illustrates another example in which the myogenic potential sensor for detecting blinking is arranged at the forehead contact unit 102. In the examples which are illustrated in FIGS. 8 and 9, it is configured such that two detection electrodes 801 and 802 share the reference electrode 803. In contrast to this, in the example which is illustrated in FIG. 13, a reference electrode 803L for the detection electrode 801, and a reference electrode 803R for the detection electrode 802 are individually provided without sharing the reference electrode on the left and right.

In addition, in a glasses-type configuration, a device is disclosed in PTL 2 (above described) in which a detection electrode is arranged in a nose pad, and a position of a line of sight is detected based on an eye potential signal by arranging a reference electrode at a portion coming into contact with earlobes at the tip end of a temple. When blinking is detected based on a myogenic potential signal, using the similar device configuration, a detection electrode of the nose pad takes in a potential signal which sensitively reacts to a change in a potential which is associated with a movement of an iris due to a movement of an eyeball. In addition, since the reference electrode is arranged at the rear side of the head portion which is separated from the detection electrode, and picks up brainwaves, as well, it is difficult to read a change in a potential due to the blinking. In contrast to this, according to the embodiment, since the reference electrode 803 is arranged in the vicinity of the detection electrodes 801 and 802, it is possible to prevent the brainwaves from being mixed in.

FIG. 14 schematically illustrates a configuration of a circuit 1400 which processes an output signal of the myogenic potential sensor which is illustrated in FIGS. 8 and 9. The illustrated processing circuit 1400 is mounted on the state information obtaining unit 705, for example.

A first differential amplification unit 1401 inputs a potential signal of a left eye blinking detection electrode 801 to a positive terminal, inputs a potential signal of the reference electrode 803 in a negative terminal, and performs a differential amplification with respect to a difference thereof. In addition, a first filter 1403 is configured by a band pass filter, a notch, or the like, however, the filter eliminates an unnecessary component which is included in a differential amplification signal output from the first differential amplification unit 1401, and outputs the signal to a determination unit 1405 thereafter.

In addition, a second differential amplification unit 1402 inputs a potential signal of a right eye blinking detection electrode 802 to a positive terminal, inputs a potential signal of the reference electrode 803 in a negative terminal, and performs a differential amplification with respect to a difference thereof. In addition, a second filter 1404 is configured by a band pass filter, a notch, or the like, however, the filter eliminates an unnecessary component which is included in a differential amplification signal output from the second differential amplification unit 1402, and outputs the signal to the determination unit 1405 thereafter.

The determination unit 1405 detects whether or not a user intentionally blinks the left eye, the right eye, and both eyes based on potential signals $D_L$ and $D_R$ after the differential amplification which is obtained from the left eye blinking detection electrode 801 and the right eye blinking detection electrode 802, respectively.

FIG. 15 illustrates potential signals which are obtained from the left eye blinking detection electrode 801 and the right eye blinking detection electrode 802, respectively.

When a user wearing the image display device at a head portion intentionally blinks the left eye, as denoted by the reference numeral 1501, a waveform occurs in a potential signal from the detection electrode 801. In addition, a waveform having a polarity opposite to the above which is denoted by the reference numeral 1502 occurs in a potential signal from the other detection electrode 802.

In addition, when the user intentionally blinks the right eye, a waveform which is denoted by the reference numeral 1504 occurs in a potential signal from the detection electrode 802. In addition, a waveform having a polarity opposite to the above which is denoted by the reference numeral 1502 occurs in a potential signal from the other detection electrode 801.

In addition, when the user intentionally blinks both eyes, a waveform which is denoted by the reference numeral 1505 occurs in a potential signal from the detection electrode 801. In addition, a waveform having a polarity which is the same as the above denoted by the reference numeral 1506 occurs in a potential signal from the other detection electrode 802.

When potential signals from the detection electrodes 801 and 802 are input, the determination unit 1405 is able to determine any blinking of only the left eye blinking, only the right eye blinking, and simultaneous blinking in both eyes is performed by comparing the signal levels to respective threshold values $TH_L$ and $TH_R$. In addition, the determination unit 1405 may perform the determination based on acceleration and a speed denoting steepness of the waveform, not only the threshold value of the signal level, in order to accurately determine a waveform of the myogenic potential of blinking. In addition, when receiving a determination result of blinking from the determination unit 1405, the control unit 701 is able to perform a predetermined UI operation based on the result. However, detailed descriptions of the UI operation will be made later.

In addition, a human being regularly performs unconscious blinking, periodically. However, a myogenic potential which is generated due to the unconscious blinking is a much lower level than a myogenic potential in intentional blinking, and has a mild waveform. FIG. 16 illustrates a myogenic potential level in the intentional blinking, and a myogenic potential level in the unconscious blinking by overlapping with each other.

In addition, while a user who is wearing the image display device at a head portion performs a UI operation due to blinking, a change in the myogenic potential usually occurs due to a muscular movement in other portions of a human body, as well. However, since a myogenic potential which is generated in a place which is a lower portion than a neck is separated from the detection electrodes 801 and 802, and becomes a low signal level by being attenuated while reaching the detection electrodes 801 and 802, it is considered that the myogenic potential does not influence a determination of the determination unit 1405. In addition, it is also considered that the myogenic potential generated in the place which is the lower portion than the neck is attenuated while passing the thin neck.

FIG. 17 illustrates a processing procedure for determining blinking in the left eye using a flowchart based on the potential signal $D_L$ which is taken in from the detection electrode 801, in the determination unit 1405. In addition, the same processing procedure can be applied to the potential signal which is taken in from the detection electrode 802.

The determination unit 1405 compares a signal level of the potential signal $D_L$ to the threshold value $TH_L$, first (step S1701).

When the signal level of the potential signal $D_L$ is lower than the threshold value $TH_L$ (No in step S1701), the determination unit 1405 determines that the blinking is not the left eye blinking.

On the other hand, when the signal level of the potential signal $D_L$ is higher than the threshold value $TH_L$ (Yes in step S1701), the determination unit 1405 obtains time differential or time difference of a signal value of the potential signal $D_L$, obtains a speed of the signal value (step S1702), and checks whether or not the speed is in a range of a predetermined value [V1, V2] (step S1703).

When the speed of the signal value is out of the range of the predetermined value [V1, V2] (No in step S1703), the determination unit 1405 determines that the blinking is not the left eye blinking.

On the other hand, when the speed of the signal value of the potential signal $D_L$ is in the range of [V1, V2] (Yes in step S1703), the determination unit 1405 obtains time differential or time difference of the speed of the signal value, obtains an acceleration of the signal value (step S1704), and checks whether or not the acceleration is in a range of a predetermined value [A1, A2] (step S1705).

When the speed and acceleration of the signal value is out of the range of the predetermined value [A1, A2] (No in step S1705), the determination unit 1405 determines that the blinking is not the left eye blinking. On the other hand, when the acceleration of the signal value of the potential signal $D_L$ is in the range of [A1, A2] (Yes in step S1705), the determination unit 1405 determines that the left eye blinking is performed (step S1706), and outputs the determination result to the control unit 701.

In addition, in a myogenic potential which is generated when performing the intentional blinking, there is an individual difference in each user. Accordingly, in order for the determination unit 1405 to make an accurate determination on the blinking, it is considered that learning processing for accurately setting the threshold values $TH_L$ and $TH_R$ of the left and right eyes blinking, a speed denoting steepness of a waveform, and acceleration is necessary. For example, it is possible to perform the learning of the threshold values $TH_L$ and $TH_R$ in each user, the speed [V1, V2], and the acceleration [A1, A2] by causing a user to perform a plurality of blinking operations of both eyes alternately, and by performing statistical processing such as averaging of myogenic potential levels which are obtained during the blinking operations.

It is preferable that the learning of the threshold values $TH_L$ and $TH_R$ be performed when a user starts to use the image display device. For example, a head-mounted display which causes a user to accurately perform adjusting of the eye width by displaying a signal pattern for adjusting the eye width, when starting the use has been proposed (for example, refer to PTL 5). For example, the learning of the threshold values $TH_L$ and $TH_R$ may be performed by displaying a message such as "Please perform left eye blinking N times", or "Please perform right eye blinking N times" after performing the adjusting of the eye width when setting up the device, by causing the user to perform blinking in each eye, and by measuring a myogenic potential during the time.

In addition, the learning result of the threshold values $TH_L$ and $TH_R$, the speed [V1, V2], and the acceleration {A1, A2} in each user is maintained in the state information obtaining unit 705, or is stored in the ROM 701A (however, a case of memory device which is able to perform rewriting like EEPROM), or the RAM 701B.

[C. UI Operation Using Blinking of User]

According to the UI operation using blinking of a user, three inputs of blinking only in the left eye, blinking only in the right eye, and simultaneous blinking in both eyes is possible. For example, it is possible to allocate a UI operation such as a cursor movement in the left direction for the blinking only in the left eye, and an UI operation such as a cursor movement in the right direction for the blinking only in the right eye, respectively. The UI operation in which the cursor moves to the left in the left eye blinking, and the cursor moves to the right in the right eye blinking is easy for a user to intuitively understand thereof.

FIG. 18 illustrates a state in which a cursor position moves to the left one by one in every left eye blinking on a menu bar which is displayed on the display panel 709. In addition, FIG. 19 illustrates a state in which a cursor position moves to the right one by one in every right eye blinking on the menu bar. In FIGS. 18 and 19, menu items on which the cursor is placed are denoted by a thick line. When repeating the left eye blinking and the right eye blinking a plurality of times, the cursor position moves to the left, or to the right by the number of repeated times. Naturally, the left eye blinking and the right eye blinking may be alternately performed, and the cursor position moves according to the number of times of blinking in the respective left and right eyes.

In addition, it is possible to allocate a UI operation in which the simultaneous blinking in both eyes is selected in the current cursor position. FIG. 20 illustrates a state in which the current cursor position on the menu bar is selected due to the simultaneous blinking in both eyes. In FIG. 20, the selected menu is switched to a reversed display (or, highlighted display), and is denoted as a selected state. In addition, when only the left eye blinking, or only the right eye blinking is performed in the selected state, the selected state may be released.

Here, when the menu which is selected by the simultaneous blinking in both eyes includes a plurality of menu items, as illustrated in FIG. 21, a list of the menu items is displayed by being pulled down. As illustrated in FIG. 22, the cursor goes downward in each left eye blinking on the pulldown menu. In addition, as illustrated in FIG. 23, the cursor returns to the upper part in each right eye blinking. Alternatively, the cursor may go downward in each the left eye blinking, and may return to the upper part in each the right eye blinking. In addition, due to the simultaneous blinking in both eyes, a menu item at a current cursor position is selected on the pulldown menu. In addition, as illustrated in FIG. 24, the selected menu is switched to a reversed display (or highlighted display), and is denoted as a selected state. In addition, when only the left eye blinking, or only the right eye blinking is performed in the selected state, the selected state may be released.

In addition, it is possible to confirm the selected state of the menu item by performing the blinking in both eyes twice in a row. Since the blinking in both eyes twice in a row reminds a user a double click of a mouse, it is easy for the user to intuitively understand the confirming of the selection. FIG. 25 illustrates an example of a reproduction menu screen of video contents. In the figure, a cursor is placed on a reproducing button through only the left eye blinking, or only the right eye blinking, and is in a selected state. At this time, the selection of the reproducing button is confirmed by performing the blinking in both eyes twice in a row, and the reproducing process of the video contents is started. Naturally, if the blinking in both eyes is performed twice in a row when a button for fast-forwarding, rewinding, a pause, a reproduction stop, or the like is in a selected state, the processing is started similarly.

The control unit 701 is able to perform the UI operations which are illustrated in FIGS. 18 to 25 based on the blinking detection results in the left and right eyes which are obtained in the state information obtaining unit 705.

[D. Application to Information Input Device]

The embodiment to which the technology disclosed in the specification is applied to the head-mounted image display device has been described. That is, it is an embodiment in which the image display device is operated using a UI operation based on blinking of a user which is obtained from an output result of a myogenic potential sensor including the detection electrodes 801 and 802, and the reference electrode 803, and an operation target using the blinking is the image display device itself.

The technology which is disclosed in the specification is not limited to the image display device, and it is also possible to apply the technology to an input device for operating an external device such as a personal computer, a video reproducing device, or the like, using a UI.

FIG. 26 illustrates an inner configuration example of the information input device 2600 to which the technology disclosed in the specification is applied. Though it is not illustrated, the information input device 2600 is used by being mounted on a head portion of a user who uses a personal computer, a video reproducing device, or the like, similarly to a hat shaped structure body which is illustrated in FIGS. 1 to 6, for example, and has portions which come into close contact with the vicinity of the left and right eyes, such as a forehead of the user. Hereinafter, each unit will be described.

A control unit 2601 includes a ROM 2601A, or a RAM 2601B. A program code which is executed in the control unit 2601, or various data items are stored in the ROM 2601A. The control unit 2601 performs an overall control of the entire operation of the device 2600 including a UI operation, by executing a program which is loaded into the RAM 2601B.

A blinking detection unit 2602 includes a myogenic potential sensor, and a processing circuit which processes an output signal of the myogenic potential sensor. The myogenic potential sensor is configured by a pair of blinking detection electrodes 801 and 802 which come into contact with the left and right eyes at approximately right above the eyes (or, approximately right below), and a reference electrode 803 which is arranged in approximately a center portion of both the detection electrodes 801 and 802 which are similar to those illustrated in FIG. 8. In addition, the processing circuit which processes the output signal of the myogenic potential sensor has the same configuration as that in FIG. 14, processes potential signals which are output from each of the detection electrodes 801 and 802 in the same processing procedure as that in FIG. 17, and detects blinking in each of the left and right eyes.

In addition, in the information input device 2600, a fact that a signal value, a speed, acceleration are considered when detecting blinking based on a potential signal which is output from each of the detection electrodes 801 and 802, or a fact that it is necessary to learn a threshold value of the signal value, a threshold value of the speed, and a threshold value of the acceleration in each user is the same as the above descriptions.

In an input-output interface 2603, external devices as targets of a UI operation such as a personal computer, a video reproducing device, and the like are connected to each other. For a mutual connection between devices, it is possible to use, for example, an MHL or a USB, a HDMI, a Bluetooth (registered trade mark) communication, an infrared communication, or the like.

Though it is not illustrated, the external device such as a personal computer, a video reproducing device, or the like includes a display unit which displays a menu screen or the like, and the same UI operations which are illustrated in FIGS. 18 to 25 are performed based on three inputs of blinking only in the left eye, blinking only in the right eye, and simultaneous blinking in both eyes which are sent from the information input device 2600.

[E. Configuration of Technology Disclosed in Specification]

The technology which is disclosed in the specification also can have the following configurations.

(1) An information processing device, including at least one electrode configured to generate at least one signal related to eye blinking of a subject; and a processing circuit configured to receive the at least one signal and detect eye blinking of the subject based on the at least one signal.

(2) The device as recited in (1), wherein the at least one signal is indicative of at least one myogenic potential related to eye blinking.

(3) The device as recited in (1), wherein the at least one electrode includes a first electrode placed in proximity to a right eye of the subject, and a second electrode placed in proximity to a left eye of the subject.

(4) The device as recited in (3), wherein the at least one electrode further includes a reference electrode placed near a midpoint between the first electrode and the second electrode.

(5) The device as recited in (4), wherein the reference electrode is arranged in the vicinity of the first electrode and the second electrode.

(6) The device as recited in (3), wherein the first electrode is placed approximately above or approximately below the right eye of the subject, and the second electrode is placed approximately above or approximately below the left eye of the subject.

(7) The device as recited in (1), wherein the processing circuit is configured to detect eye blinking by performing at least one operation on the at least one signal to generate at least one processed signal and comparing the at least one processed signal to at least one of a threshold, a range of signal velocities, and a range of signal accelerations.

(8) The device as recited in (7), wherein at least one of the threshold, the range of signal velocities, and the range of signal accelerations is determined according to a learning process.

(9) The device as recited in (1), wherein the processing circuit is configured to detect eye blinking by amplifying the at least one signal to generate at least one amplified signal, filtering the at least one amplified signal to generate at least one filtered signal, and comparing the at least one filtered signal to at least one of a threshold, a range of signal velocities, and a range of signal accelerations.

(10) The device as recited in (1), wherein the device is operable to detect a blinking of a left eye only, a blinking of a right eye only, and a simultaneous blinking of a right eye and a left eye.

(11) The device as recited in (1), wherein the device is incorporated in a head mounted display.

(12) The device as recited in (11), wherein the at least one electrode is incorporated in a forehead contact unit of the head mounted display.

(13) The device as recited in (12), wherein the forehead contact unit is adjustable.

(14) The device as recited in (1), wherein the at least one electrode includes at least one of a conductive gel electrode, a dry electrode, and a non-contact type capacity coupling electrode.

(15) The device as recited in (1), wherein the processing circuit is configured to control operation of a display based on detected eye blinking.

(16) The device as recited in (15), wherein the display is configured to display a menu, and detected blinking of a left eye causes a designation within the menu to move in a right-to-left direction.

(17) The device as recited in (15), wherein the display is configured to display a menu, and detected blinking of a right eye causes a designation within the menu to move in a left-to-right direction.

(18) The device as recited in (15), wherein the display is configured to display a menu, and detected simultaneous blinking of a left eye and a right eye causes selection of a menu item.

(19) The device as recited in (15), wherein the display is configured to display a menu, and detected simultaneous blinking of a left eye and a right eye, twice in succession, causes confirmation of selection of a menu item.

(20) An information processing method, including obtaining at least one signal related to eye blinking of a subject; and detecting eye blinking of the subject based on the at least one signal.

(21) A non-transitory computer-readable medium storing a computer-readable program for implementing an information processing method, the method including obtaining at least one signal related to eye blinking of a subject; and detecting eye blinking of the subject based on the at least one signal.

(22) An information processing device, including a first electrode placed in proximity to a left eye of a subject; a second electrode placed in proximity to a right eye of the subject; a reference electrode placed near a midpoint between the first electrode and the second electrode; and a processing circuit configured to detect eye blinking of the subject based on a first signal obtained from the first electrode and the reference electrode, and a second signal obtained from the second electrode and the reference electrode.

(23) A display apparatus, including a display; at least one electrode configured to generate at least one signal related to eye blinking of a subject; and a processing circuit configured to receive the at least one signal and detect eye blinking of the subject based on the at least one signal, and to control the display based on the detected eye blinking of the subject.

The technology which is disclosed in the specification also can have the following configuration.

(1) An image display device which includes a display unit, a blinking detection unit which detects the blinking of a user, and a control unit which performs a control corresponding to the blinking which is detected by the blinking detection unit.

(2) The image display device which is disclosed in (1), in which the blinking detection unit includes a first detection electrode which is arranged in the vicinity of a left eye of the user; a second detection electrode which is arranged in the vicinity of a right eye of the user; and a reference electrode which is arranged in approximately a center portion between the first detection electrode and the second detection electrode, and in which blinking operations of the left eye and right eye are detected based on a combination of a first potential signal which is obtained between the first detection electrode and the reference electrode and a second potential signal which is obtained between the second detection electrode and the reference electrode.

(3) The image display device which is disclosed in (2), in which the blinking detection unit suppresses an influence of an eye potential which is caused by a movement of an iris by arranging the first detection electrode and the second detection electrode approximately right above, or approximately right below the left eye and the right eye, respectively.

(4) The image display device which is disclosed in (2), in which the blinking detection unit offsets an eye potential which is associated with a movement of an iris of the left eye, and an eye potential which is associated with a movement of an iris of the right eye by arranging the reference electrode at a place where a distance from the left eye and a distance from the right eye become approximately the same.

(5) The image display device which is disclosed in (2), in which the blinking detection unit suppresses an influence of brainwaves of the user by arranging the reference electrode at a place which is close from the first and second detection electrodes.

(6) The image display device which is disclosed in (2), in which the blinking detection unit detects each blinking of the left eye and right eye by comparing the first detection electrode which is arranged in the vicinity of the left eye of the user, threshold values of signal values of the first potential signal and the second potential signal, a threshold value of changing speed of the potential signal, and a threshold value of acceleration with each other.

(7) The image display device which is disclosed in (6), in which the blinking detection unit learns a threshold value of a signal value of a potential signal which is used when detecting blinking in each user, the threshold value of changing speed of the potential signal, and the threshold value of acceleration.

(8) The image display device which is disclosed in (1), in which the control unit performs a UI operation with respect to a display screen of the display unit according to the blinking which is detected by the blinking detection unit.

(9) The image display device which is disclosed in (8), in which the control unit performs the UI operation corresponding to the blinking only in the left eye, the blinking only in the right eye, and the blinking in both eyes, respectively.

(10) The image display device which is disclosed in (8), in which the control unit selects a cursor movement to a left direction in each blinking of only the left eye, a cursor movement to a right direction in each blinking of only the right eye, and a current cursor position corresponding to the blinking in both eyes on the display screen.

(11) An information input device which is used by being mounted on a head portion of a user includes a blinking detection unit detecting blinking operations in left and right eyes of the user; and an interface which outputs input operation information corresponding to the blinking operations which are detected by the blinking detection unit to the outside.

(12) The information input device which is disclosed in (11), in which the blinking detection unit includes a first detection electrode which is arranged in the vicinity of the left eye of the user; a second detection electrode which is arranged in the vicinity of the right eye of the user; and a reference electrode which is arranged in approximately a center portion between the first detection electrode and the second detection electrode, and detects blinking operations of the left eye and right eye based on a combination of a first potential signal which is obtained between the first detection electrode and the reference electrode and a second potential signal which is obtained between the second detection electrode and the reference electrode.

(13) The information input device which is disclosed in (12), in which the blinking detection unit suppresses an influence of an eye potential which is caused by a movement of an iris by arranging the first detection electrode and the second detection electrode approximately right above, or approximately right below the left eye and the right eye, respectively.

(14) The information input device which is disclosed in (12), in which the blinking detection unit offsets an eye potential which is associated with a movement of an iris of the left eye, and an eye potential which is associated with a movement of an iris of the right eye by arranging the reference electrode at a place where a distance from the left eye and a distance from the right eye become approximately the same.

(15) The information input device which is disclosed in (12), in which the blinking detection unit suppresses an influence of brainwaves of the user by arranging the reference electrode at a place which is close to the first and second detection electrodes.

(16) The information input device which is disclosed in (12), in which the blinking detection unit detects each blinking of the left eye and right eye by comparing the first detection electrode which is arranged in the vicinity of the left eye of the user, threshold values of signal values of the first potential signal and the second potential signal, a threshold value of changing speed of the potential signal, and a threshold value of acceleration with each other.

(17) The information input device which is disclosed in (16), in which the blinking detection unit learns a threshold value of a signal value which is used when detecting blinking in each user, the threshold value of changing speed of the potential signal, and the threshold value of acceleration.

(18) The information input device which is disclosed in (11), in which the input operation information corresponding the blinking only in the left eye, the blinking only in the right eye, and the blinking in both eyes, respectively, are output from the interface.

(19) The information input device which is disclosed in (11), in which the UI operation information which issues instructions of a movement to the left direction in each blinking of only in the left eye, a movement to the right direction in each blinking of only in the right eye, and a selection of a current position corresponding to the blinking in both eyes, respectively, are output from the interface.

(20) An image display device which includes a display unit, a potential signal detection unit which detects a potential signal in the vicinity of eyes of a user, and a control unit which performs a control corresponding to a detection result of the potential signal detection unit.

The present disclosure contains subject matter related to that disclosed in Japanese Priority Patent Application JP 2012-243065 filed in the Japan Patent Office on Nov. 2, 2012, the entire contents of which are hereby incorporated by reference.

It should be understood by those skilled in the art that various modifications, combinations, sub-combinations and alterations may occur depending on design requirements and other factors insofar as they are within the scope of the appended claims or the equivalents thereof.

INDUSTRIAL APPLICABILITY

As described above, the technology which is disclosed in the specification has been described in detail with reference to specified embodiments. However, it is obvious that persons skilled in the art may perform a modification or substitution of the embodiment without departing from the scope of the technology which is disclosed in the specification.

A head-mounted image display device can be classified into a light shielding type and a transmission type, and embodiments relating to the light shielding type head-mounted image display device has been mainly described in the specification. However, naturally, it is possible to apply the technology disclosed in the specification to a device of the transmission type, similarly.

In addition, the technology disclosed in the specification is not limited to a case of being integrally configured with the image display device, and can be used in a video reproducing operation, or an input operation of a personal computer or the like, by being configured as an information input device based on blinking of a user.

In short, the technology which is disclosed in the specification has been described using a form of exemplification, and is not construed by limiting to the embodiments. In order to determine the scope of the technology disclosed in the specification, claims will be referred to.

REFERENCE SIGNS LIST

102 Forehead contact unit
103 Nose contact unit
104 Upper band
105 Lower band
141 Tact switch
142 Rotation shaft
143 Arm
144 Spring
701 Control unit
701A ROM
701B RAM
702 Input operation unit
703 Remote control reception unit
704 Environment information obtaining unit
705 State information obtaining unit
706 Communication unit
707 Image processing unit
708 display driving unit
709 display panel
710 Virtual image optical unit
801, 802 Blinking detection electrode
803 Reference electrode
2600 Information input device
2601 Control unit
2601A ROM
2601B RAM
2602 Blinking detection unit
2603 Input-output interface

The invention claimed is:

1. A light shielding head-mounted image display device, comprising: at least one electrode configured to generate at least one signal related to eye blinking of a subject; and a processing circuit configured to (i) receive the at least one signal, (ii) detect eye blinking of the subject based on the at least one signal, and (iii) cause an input operation, based on detected eye blinking of the subject, to be performed in the light shielding head-mounted image display device, the at least one electrode includes a first electrode, a second electrode, a reference electrode and another reference electrode, and the processing circuit is configured to detect the eye blinking of the subject based on (i) a first differential signal obtained from a difference between a first signal from the first electrode and a reference signal from the reference between a second signal from the second electrode and another reference signal from the another reference electrode.

2. The device as recited in claim 1, wherein the at least one signal is indicative of at least one myogenic potential related to eye blinking.

3. The device as recited in claim 1, wherein the at least one electrode comprises the first electrode placed in proximity to a right eye of the subject, and the second electrode placed in proximity to a left eye of the subject.

4. The device as recited in claim 3, wherein the first electrode is placed approximately above or approximately below the right eye of the subject, and the second electrode is placed approximately above or approximately below the left eye of the subject.

5. The device as recited in claim 1, wherein the device is operable to detect a blinking of a left eye only, a blinking of a right eye only, and a simultaneous blinking of a right eye and a left eye.

6. The device as recited in claim 1, wherein the at least one electrode is incorporated in a forehead contact unit.

7. The device as recited in claim 6, wherein the forehead contact unit is adjustable.

8. The device as recited in claim 1, wherein the at least one electrode comprises at least one of a conductive gel electrode, a dry electrode, and a non-contact type capacity coupling electrode.

9. The device as recited in claim 1, wherein the input operation is a display operation on a display such that the processing circuit is configured to perform the display operation based on the detected eye blinking.

10. The device as recited in claim 9, wherein the display is configured to display a menu, and the detected blinking of a left eye causes a designation within the menu to move in a right-to-left direction.

11. The device as recited in claim 9, wherein the display is configured to display a menu, and the detected blinking of a right eye causes a designation within the menu to move in a left-to-right direction.

12. The device as recited in claim 9, wherein the display is configured to display a menu, and the detected simultaneous blinking of a left eye and a right eye causes selection of a menu item.

13. The device as recited in claim 9, wherein the display is configured to display a menu, and detected simultaneous blinking of a left eye and a right eye, twice in succession, causes confirmation of selection of a menu item.

14. An information processing method for use with a light shielding head-mounted image display device, said method comprising: obtaining a first signal from a first detection electrode and a reference signal from a reference electrode related to the eye blinking of a subject; obtaining a second signal from a second detection electrode and another reference signal from another reference electrode related to the eye blinking of a subject; detecting eye blinking of the subject based on (i) a first differential signal obtained from a difference between the first signal from the first electrode and the reference signal from the reference electrode and (ii) a second differential signal obtained from a difference between the second signal from the second detection electrode and another reference signal from the another reference electrode, and causing an input operation, based on detected eye blinking of the subject, to be performed in the light shielding head-mounted image display device.

15. A non-transitory computer-readable medium storing a computer-readable program for implementing an information processing method for use with a light shielding head-mounted image display device, the method comprising: obtaining a first signal from a first detection electrode and a reference signal from a reference electrode related to the eye blinking of a subject; obtaining a second signal from a second detection electrode and another reference signal from another reference electrode related to the eye blinking of a subject; detecting eye blinking of the subject based on (i) a first differential signal obtained from a difference between the first signal from the first electrode and the reference signal from the reference electrode and (ii) a second differential signal obtained from a difference between the second signal from the second detection electrode and another reference signal from the another reference electrode, and causing an input operation, based on detected eye blinking of the subject, to be performed in the light shielding head-mounted image display device.

* * * * *